(12) United States Patent
Hunter

(10) Patent No.: US 11,821,224 B1
(45) Date of Patent: Nov. 21, 2023

(54) METHOD AND APPARATUS FOR PROVIDING RESIDENTIAL HOUSING ASSISTED CARE AND PREVENTATIVE HEALTHCARE

(71) Applicant: Mark A. Hunter, Afton, WY (US)

(72) Inventor: Mark A. Hunter, Afton, WY (US)

( * ) Notice: Subject to any disclaimer, the term of this patent is extended or adjusted under 35 U.S.C. 154(b) by 0 days.

(21) Appl. No.: 16/893,277

(22) Filed: Jun. 4, 2020

Related U.S. Application Data

(60) Provisional application No. 62/857,257, filed on Jun. 4, 2019.

(51) Int. Cl.
| | |
|---|---|
| *E04H 1/02* | (2006.01) |
| *A61B 5/00* | (2006.01) |
| *E04B 1/343* | (2006.01) |
| *E04H 9/14* | (2006.01) |
| *E04H 3/08* | (2006.01) |

(52) U.S. Cl.
CPC ............ *E04H 1/02* (2013.01); *A61B 5/0022* (2013.01); *E04B 1/34336* (2013.01); *E04H 3/08* (2013.01); *E04H 9/145* (2013.01)

(58) Field of Classification Search
CPC ........... E04H 3/08; E04H 1/02; A61B 5/0022; E04B 1/34336; B60S 9/00; B60S 9/02; B60S 9/04; B60S 9/06; B60S 9/08; B66F 3/08; B66F 5/025; B66F 7/025; B66F 7/0608; B66F 2700/04
See application file for complete search history.

(56) References Cited

U.S. PATENT DOCUMENTS

| | | | | |
|---|---|---|---|---|
| 124,251 | A * | 3/1872 | Cartwright | ................ B60S 9/04 188/38 |
| 2,677,571 | A * | 5/1954 | Williams | .................. B60P 3/32 280/789 |
| 3,711,118 | A * | 1/1973 | Kirwan | ..................... B60S 9/22 280/763.1 |

(Continued)

OTHER PUBLICATIONS

Meinhold, Oct. 8, 2010, https://inhabitat.com/floating-container-houses-proposed-for-pakistan-flood/amphibious-container-1/.*

*Primary Examiner* — Brian E Glessner
*Assistant Examiner* — Adam G Barlow
(74) *Attorney, Agent, or Firm* — Laurence B. Bond

(57) ABSTRACT

A method and apparatus for providing residential care and health is disclosed. The method includes providing a residential unit which is transported to a location proximate a residence of a primary health provider. The residential unit is then positioned on a plurality of height adjustable pads which function to retain the residential unit in place and substantially restrict any horizontal movement of the residential unit relative to the underlying ground. The resident is then introduced into the residential unit. The unit is fitted with telemetric monitoring equipment adapted to monitor and relay information regarding the resident's health, vital signs, movement to a remotely located care provider. Upon the resident obtaining a condition which no longer requires the monitoring of his health and vital signs, the residential unit is transported away from the location. The residential unit includes a metal frame coupled to an enclosure which defines an interior and an air-sealed door which accesses the interior.

32 Claims, 22 Drawing Sheets

(56) References Cited

U.S. PATENT DOCUMENTS

| | | | | |
|---|---|---|---|---|
| 4,155,204 | A * | 5/1979 | Prozinski | E04B 1/34336 52/69 |
| 4,181,347 | A * | 1/1980 | Clark | A61B 6/4488 52/27 |
| 4,425,978 | A * | 1/1984 | Star | B62D 47/02 180/41 |
| 4,449,746 | A * | 5/1984 | Clark | A61G 3/001 52/27 |
| 4,711,464 | A * | 12/1987 | Bilas | B62D 61/12 180/209 |
| 4,915,435 | A * | 4/1990 | Levine | A61G 3/001 29/428 |
| 4,969,631 | A * | 11/1990 | Whittingham | B60S 9/08 254/425 |
| 5,065,462 | A * | 11/1991 | Romano | E04H 1/1216 4/662 |
| 5,409,251 | A * | 4/1995 | Thorndyke | B60S 9/12 280/475 |
| 5,755,478 | A * | 5/1998 | Kamiya | B60P 3/14 5/81.1 HS |
| 5,775,758 | A * | 7/1998 | Eberspacher | B60P 3/14 296/19 |
| 5,788,306 | A | 8/1998 | DiBagio et al. | |
| 6,247,276 | B1 * | 6/2001 | Masters | E04B 1/34347 52/169.12 |
| 6,776,451 | B2 * | 8/2004 | Crean | B60H 1/00364 296/156 |
| 7,338,109 | B1 * | 3/2008 | Crean | B60P 3/34 296/164 |
| 7,347,472 | B2 * | 3/2008 | Pellegrin, Jr. | G09B 23/28 434/262 |
| 7,614,677 | B2 * | 11/2009 | Ksiezopolski | B60J 10/30 296/171 |
| 7,794,001 | B2 * | 9/2010 | Blackwell | B60P 3/34 296/168 |
| 7,878,545 | B2 * | 2/2011 | Rhymer | B60P 3/36 280/789 |
| 8,038,593 | B2 * | 10/2011 | Friedman | H04L 67/75 600/26 |
| 8,291,648 | B1 * | 10/2012 | Orr | E04H 1/02 52/79.5 |
| 2002/0104271 | A1 * | 8/2002 | Gallant | E04B 2/7448 52/270 |
| 2005/0055759 | A1 * | 3/2005 | Cameron | B60R 15/04 4/321 |
| 2007/0007794 | A1 * | 1/2007 | Bertoch | B62D 21/20 296/168 |
| 2010/0001239 | A1 * | 1/2010 | Dufour | B66F 3/08 254/100 |
| 2016/0160515 | A1 * | 6/2016 | Wallance | E04F 10/10 52/745.02 |
| 2017/0130475 | A1 * | 5/2017 | Park | F24F 13/26 |
| 2018/0093675 | A1 * | 4/2018 | Holub | B60W 50/14 |
| 2018/0134116 | A1 * | 5/2018 | Chen | B60N 2/976 |
| 2019/0226185 | A1 * | 7/2019 | Cincotta | E04H 1/02 |
| 2022/0023787 | A1 * | 1/2022 | Huang | A61L 9/205 |

\* cited by examiner

METHOD AND APPARATUS FOR PROVIDING RESIDENTIAL HOUSING ASSISTED CARE AND PREVENTATIVE HEALTHCARE

RELATED APPLICATION

This application claims the benefit under 35 U.S.C. § 119 of U.S. Provisional Application 62/857,257 entitled METHOD AND APPARATUS FOR PROVIDING RESIDENTIAL HOUSING, ASSISTED CARE AND PREVENTIVE HEALTHCARE, filed 4 Jun. 2019. The aforesaid provisional patent application is hereby incorporated by reference in its entirety.

FIELD

This invention relates to the provision of Residential housing, care and health services. More particularly, this invention is directed to a method and apparatus for providing individualized residential housing, assisted care and preventative health services.

BACKGROUND

Provision of assisted senior care and senior healthcare is a highly volatile issue among US policymakers. Especially controversial is the provision of care to the aged and those who require some form of residential care as part of their treatment. Various legislative attempts during the 20th century have attempted, without success, to solve this problem. With the baby boomer generation now entering its retirement years, the problems associated with assisted senior housing, health care, especially residential care and health, have reached epic proportions.

While nursing homes and long term care facilities have become for many the accepted approach for dealing with the care of an aged family member, the cost of care in such facilities is oftentimes beyond the affordability of many families. Moreover, a number of other issues have arisen over the last three to four decades regarding the quality of care available in such facilities. They have high turnover of their frontline employees arising from low pay and the work load type. The new challenges of COVID-19 these long term care facilities have become the epicenter for disease transmission and death by housing multiple seniors under one roof, which is a problem with our current congregate or institutional care model are just a few. For many, the care provided by family members at home or single person centered care continues to be the preferred more affordable and lower risk approach to managing these many issues. Families are looking for new options and alternatives to house their seniors safer, more affordably and with better outcomes. Never before have new senior housing and care options been so front and center and desperately needed.

However, many families do not have the required space and tools to undertake care of a family member with mobility or other disabilities in their own homes. Moreover, the cost of retrofitting the living accommodation of an elderly person's residence to facilitate assisted senior care for a short term is oftentimes beyond that person or his or her family's financial resources or fiscally makes investment sense. There continues to be a need for an approach to provide long term residential care, especially for the aged members of our population, which at once permits the elderly of our society to age in place with dignity, facilitates the continuation and fostering of family relationships (the social connection) and allows families to render care to their elderly.

SUMMARY OF THE INVENTION

The invention discloses an apparatus and method for providing individualized assisted residential housing, care and preventive health care to an individual requiring assistance with mobility, bathing, dressing, toileting, and managing meals and medications.

The apparatus includes a residential unit having a frame assembly and an enclosure. The enclosure, which is preferably water-tight, is secured to the rigid frame to largely encase the frame and form a water tight assembly. The enclosure defines a hollow interior and a door which provides access to the interior. In a preferred aspect the door is provided with an air-tight seal and preferably a float kit adapted to seal the interior of the unit from the entry of water.

Due in part to the air-tight door, the enclosure, together with the frame, provides a structure which will float in water. Should the residential unit be subjected to flood waters, the unit is structured to provide a measure of safety to its occupant in that it will simply float on the surface of the flooding waters. As will be noted later, the residential unit is generally not fixedly secured to the ground at its use situs, but instead remains in place at that situs simply due to its weight. In high wind areas it may be tethered to the ground using screw anchors into the earth. If by chance it is placed in both high wind area and flood area these screws would have to be removed during flood warnings. It follows that upon being surrounded by flood waters, instead of remaining fixed and thereby permitting the rising waters to enter the interior of the residential unit and imperil the inhabitant, or damage (and to protect leased infrastructure) the unit is designed to float on the surface of such waters thereby contributing to the safety of the inhabitant and protection of unit.

The interior of the residential unit may be fitted with one or more types of monitoring equipment, for use in monitoring health related vital signs of the resident occupant. In a preferred aspect this monitoring equipment may include telehealth transmission means for gathering and subsequently transmitting the monitored information regarding those vital signs to a health care professional located remotely from the residential unit. The transmission means may also be adapted to transmit the monitored information to a primary health provider located proximate the location of the residential unit.

The residential unit is designed to be positioned at its locational situs on a plurality of height adjustable pads, which in turn are adapted for placement on a ground surface. In a preferred aspect each of these adjustable pads includes a ground engaging surface which is fabricated from a material having a high coefficient of friction, e.g. rubber. The pads, being simply placed on the ground surface, provide a nonpermanent mounting platform for the rigid frame and enclosure above the ground surface. Due to the choice of their material of manufacture, the pads also generally minimize, if not preclude, any horizontal movement of the metal frame and enclosure over the underlying ground surface. The weight of the residential unit is applied to the pads and the coefficient of friction of those pads creates a frictional force which resists any lateral movement of the residential unit over the pads. In an alternative aspect the residential unit may be fitted with a tether system for securing the residential unit to the underlying ground, to anchor the unit and to keep unit from being carried away thereby permitting the residential unit to float on the rising waters and consequently provide protection to the unit.

In a preferred aspect, the residential unit is fitted with sleeping accommodations, together with bathroom and kitchenette facilities, for use by its occupant/caretaker. Temporary sleeping accommodations for use by a primary health provider may also be incorporated into the residential unit. These temporary accommodations are preferably designed to retract into the structure of the residential unit to preserve an optimized amount of living space within the unit when they are not in use.

In preferred aspects of the invention, the enclosure may be fitted with a sunroof and one or more windows which provide not only a source of light for the unit's interior, but also provide the inhabitant with visual accessibility to the environment surrounding the exterior of the unit. These windows may incorporate selectable privacy glass, which permits the occupant to selectively change the tint or frost feature of the glass thereby permitting the occupant to restrict viewers from outside the residential unit from seeing into the unit.

The residential unit may also be constructed to be self-contained, e.g., to include environmental control systems such as heating, ventilation and air conditioning systems for controlling the temperature and air quality within the residential unit's interior. In preferred constructions the residential unit is designed and insulated to provide a comfortable interior living space in the face of environmental temperatures, outside of the unit ranging between minus 40 degrees Fahrenheit to 120 degrees Fahrenheit. With its own HVAC system and other required features the residential unit is also an environment for high level isolation and quarantine during pandemics or other infectious diseases. The unit also may be constructed to house its own water supply and waste disposal system, including grey and black water storage. Of particular importance, systems for receiving and storing waste water, produced within the unit, may be incorporated into the unit's construction. These provisions eliminate the need for the unit's connection to municipal water or sewage facilities at the location situs for a temporary use. Since the residential unit is designed to function on a 50 amp power supply, the unit may utilize a conventional automobile wiring harness to provide power to its various electrical apparatuses.

An important aspect of the invention is the portability of the residential unit. The unit is designed to be readily transported to a selected locational situs utilizing conventional transport means. In a preferred method, the unit may be prepared for shipment in one hour or less. Subsequent to its transportation to the selected locational; situs, the unit may be temporarily secured in place at that situs and then readily removed from that situs when the occupant obtains a condition in which the benefits of the unit are no longer required. Accordingly, the residential unit may be sized and configured for transport on a conventional flat-bed truck or flat-bed trailer. Moreover, the unit is further designed to be positioned on and retrieved from such a truck utilizing conventional loading equipment, such as a tug or fork lift. The frame of the unit may be configured to define one or more lift options using different openings dimensioned to receive the forks of a forklift to facilitate the use of a forklift to lift the unit onto a flat-bed trailer or alternatively remove the unit from that trailer. A specially designed tug and bogie combination may also be provided whereby retrieval of the residential unit from its transporting flat-bed trailer and subsequent transport to a selected location may be accomplished by a single service technician. In a preferred construction, one or both of the tug and the bogie wheels may be fitted with all wheel drive and a remote controlled means to control tug and bogie wheel movement for both power drive and steering.

The method of the invention includes first providing a residential unit, for example, of the type as previously described. In a preferred aspect, this residential unit is configured to house a single individual resident, although residential units dimensioned for housing more than one occupant are also within contemplation. Secondly, the residential unit is transported to a selected location. In a preferred aspect, this selected location is physically proximate to a primary health care provider, e.g. a family member or close friend. For example, the selected location may be physically proximate the residence of the primary health care provider. This physical proximity facilitates ready access to the individual resident by the health care provider. Thereafter, the residential unit is placed at the preselected location utilizing a plurality of height adjustable pads thereby positioning the residential unit elevationally above the underlying ground surface. The pads may be further adjusted to level the residential unit relative to the underlying ground surface. The pads may be physically secured to the residential unit.

In a preferred aspect, the residential unit is not secured to the ground by any form of permanent footer or foundation or other form of physical affixation to the ground surface other than its resting on the pads due to its weight. The method therefore provides for a residential unit being non-permanently installed at a location, i.e. the residential unit may be subsequently removed from the location with a modest amount of effort.

In an alternative aspect, a tie down system may be employed at this juncture to secure the residential unit to the ground surface. This alternative approach is typically utilized in locations where the residential unit may be subjected to high winds or other environmental phenomena which may result in the application of extraordinary or unusual forces being applied to the residential unit. The tie down system may utilize the openings of the unit's frame which are otherwise adapted to permit the use of fork lifts to lift and transport the unit. Tethers, in association with screw fitted anchor bolts, secured to the tethers may be connected to the unit frame using the openings.

The construction of the residential unit is sufficiently simple that its installation may be accomplished within approximately an hour by a single installation technician using a powered tug and bogie wheel assembly. Due to its construction, the unit does not require the services of a contractor, plumber, or excavator to ensure its installation.

After the residential unit is installed, the resident individual is introduced into the residential unit. Thereafter, the vital signs and general well-being of the individual are selectively monitored by either a health care professional, located physically remote from the residential unit, or by the primary health care provider, located nearby, or both, through means of at least one telemonitoring apparatus, housed within the residential unit. The results of this monitoring effort may be transmitted either in real time or at preselected time intervals consistent with the indications of the relevant health care providers via the Internet or other transmission means. The telemonitoring apparatus may include not only medical apparatus but also monitoring cameras or sensors which will permit a primary health care provider as well as a health care professional to monitor the activity of the occupant.

In the event medical care is required, such care may be provided to the resident individual within the residential unit by either the remotely based telehealth care professional, the on-site primary health care provider or a combination of the health care professional and the primary health care provider.

When the resident individual obtains a health status which no longer requires the benefits provided by the residential unit, the unit is simply removed from the locational situs, using the same means which were employed originally to transport the unit to the locational situs. Given its use of the installation pads, the unit creates a very small footprint on the ground surface of the installation situs. When the unit is removed, at most only a modest imprint may be left at the situs. The residential unit may then be transported back to the residential unit provider.

The nature of the residential unit and the described method of its use, provides a method of providing individualized residential care for patients requiring assisted living and preventive healthcare. Since the residential unit may be readily refurbished for subsequent use by further patient occupants upon its return to the residential unit provider by a first patient, a further method of use of the residential unit wherein the residential unit is leased to its patient user instead of being purchased by him/her becomes highly practicable. Moreover, since the residential unit may be transported to almost any location, the method of the unit's use provides the ability to provide residential care almost anywhere. 70% of seniors live in rural or suburban areas in the United States.

Because the residential unit does not utilize a fixed foundational base, but instead relies on a temporary placement on the ground utilizing friction pads, which may be secured to the underside of the unit, the residential unit readily meets applicable governmental zoning regulations which would otherwise preclude the use of fixed foundation supported accessory dwelling unit being positioned proximate a residential dwelling. For example, in many instances the inventive residential unit may be installed on the driveway or in the yard of a conventional residential dwelling without violating applicable city zoning ordinances. Moreover, the absence of ownership removes the concern of unit staying indefinitely, not having a fixed foundation for the residential unit, no sewer or water hookup requirements, and with patient receiving status of a "physician documented medical need" permits the provision of such a unit to easier obtain temporary zoning approval. Also for a patient to qualify for lease reimbursement the unit must be a "physician documented medical need". Medicare/Medicaid, and commercial insurance rules and regulations as a medical device which may be provided to a patient under a doctor's prescription (becoming a temporary-needed durable medical device). Furthermore, the fact that the residential unit is portable, temporary, reusable, absence of ownership, lacking a fixed foundation, and no sewer/water hookups for the residential unit may also cause the costs of such a residential unit to be covered under traditional insurance policies whereas a purchased/owned and fixed foundation structure would not qualify as it becomes real property that is attached.

In view of these considerations, the instant invention also includes a method of providing individualized residential assisted housing, care, and healthcare to a patient which includes the steps of providing a residential unit to a patient requiring assisted living and preventive healthcare and monitoring, either through leasing or purchase; subsequently transporting such residential unit to a selected location, which may be proximate a primary health care provider. Thereafter, positioning the residential unit at the selected location without securing the residential unit to the underlying ground surface by means of a fixed, ground secured foundation. Introducing the patient into the residential unit. Providing monitoring of health related vital signs, providing assisted care devices (ADA toilet, shower, bed, kitchenette and overall care environment) to the patient during their residency in the residential unit. Communicating information regarding that monitoring to a remotely located health care professional and subsequently removing the residential unit from the selected location upon the patient's obtaining a condition in which the benefits of the residential unit are no longer desired or needed.

DETAILED DESCRIPTION OF THE ILLUSTRATED EMBODIMENT

Figure 1:
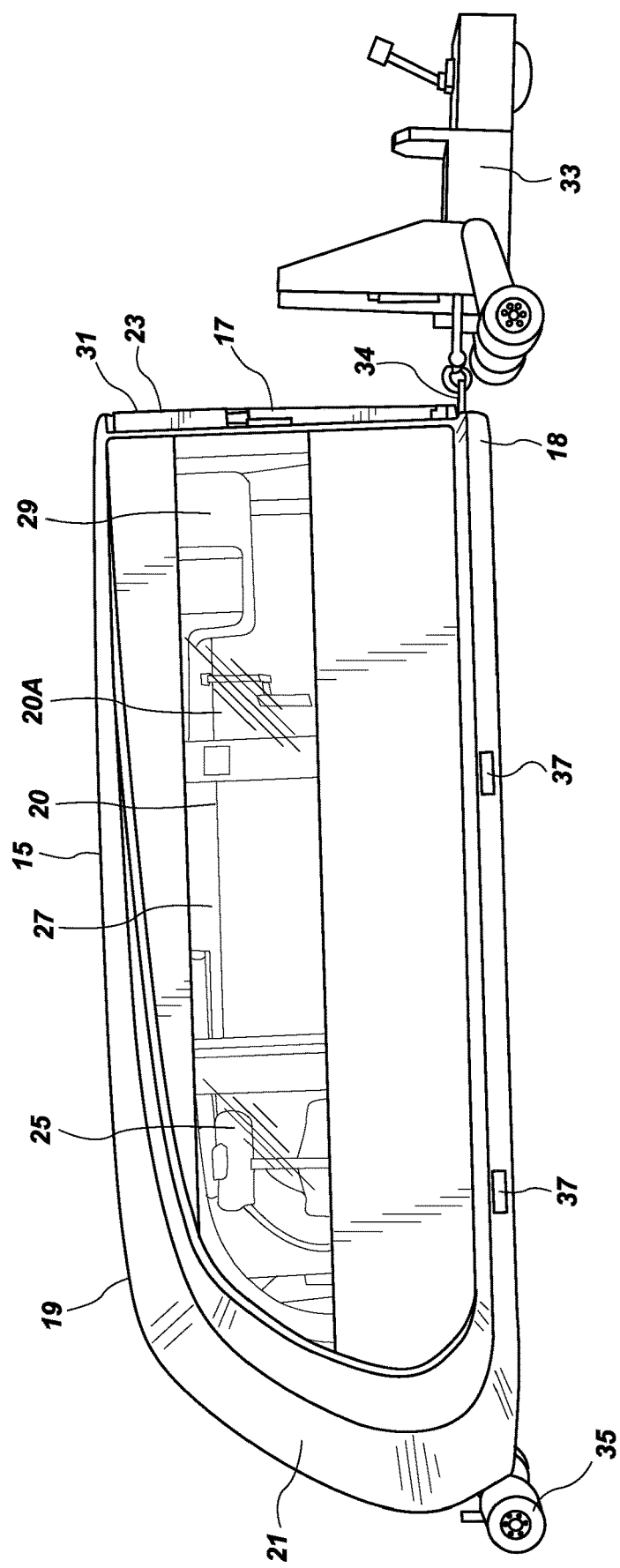
FIG. 1 is a side view of a residential unit of the invention.
Figure 1A:
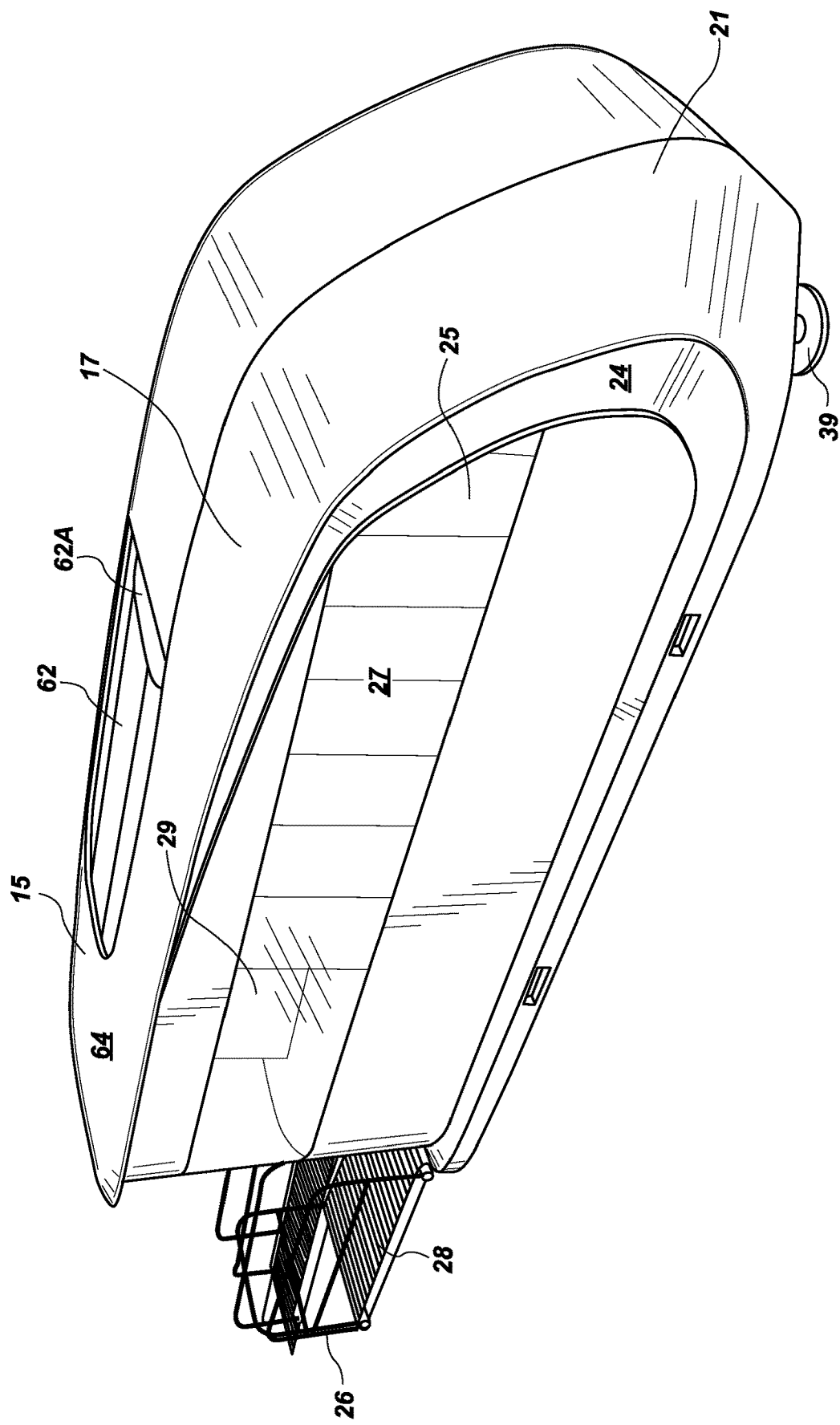
FIG. 1A is a perspective rear view of the residential unit of FIG. 1.
Figure 1B:
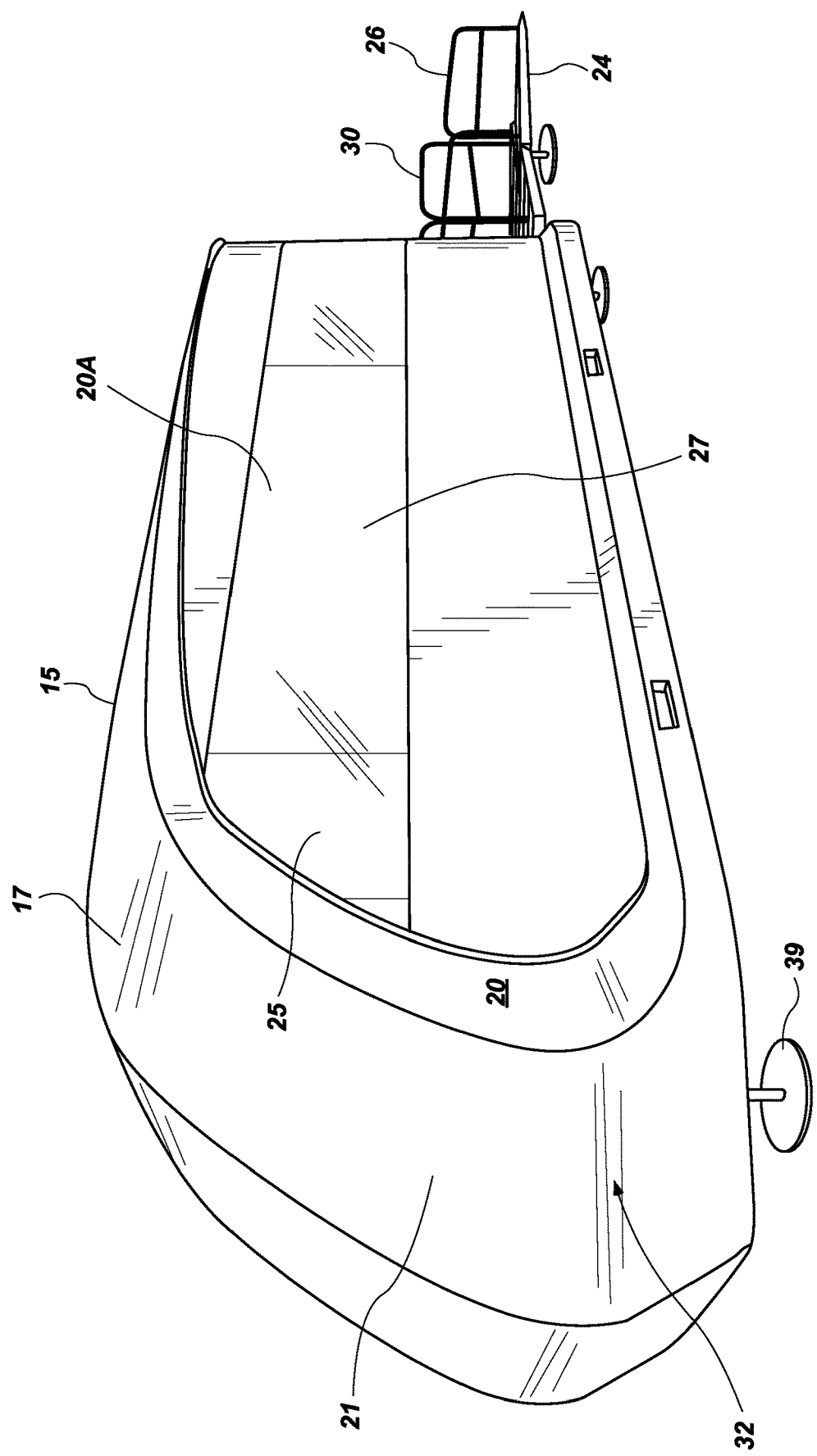
FIG. 1B is a another perspective rear view of the residential unit of FIG. 1.
Figure 1C:
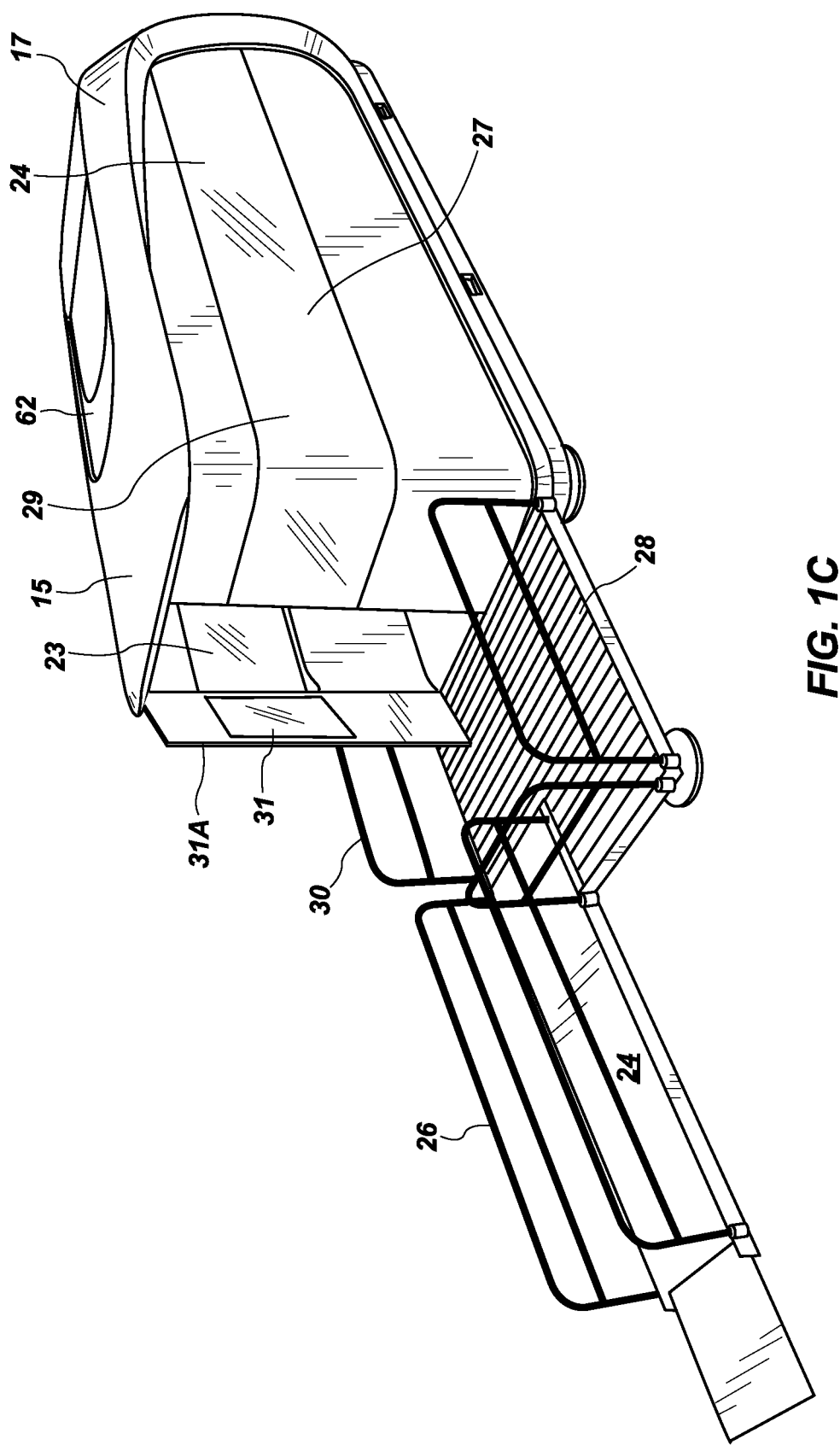
FIG. 1C is a front perspective view of the residential unit of FIG. 1 with the deck in a deployed condition.
Figure 1D:
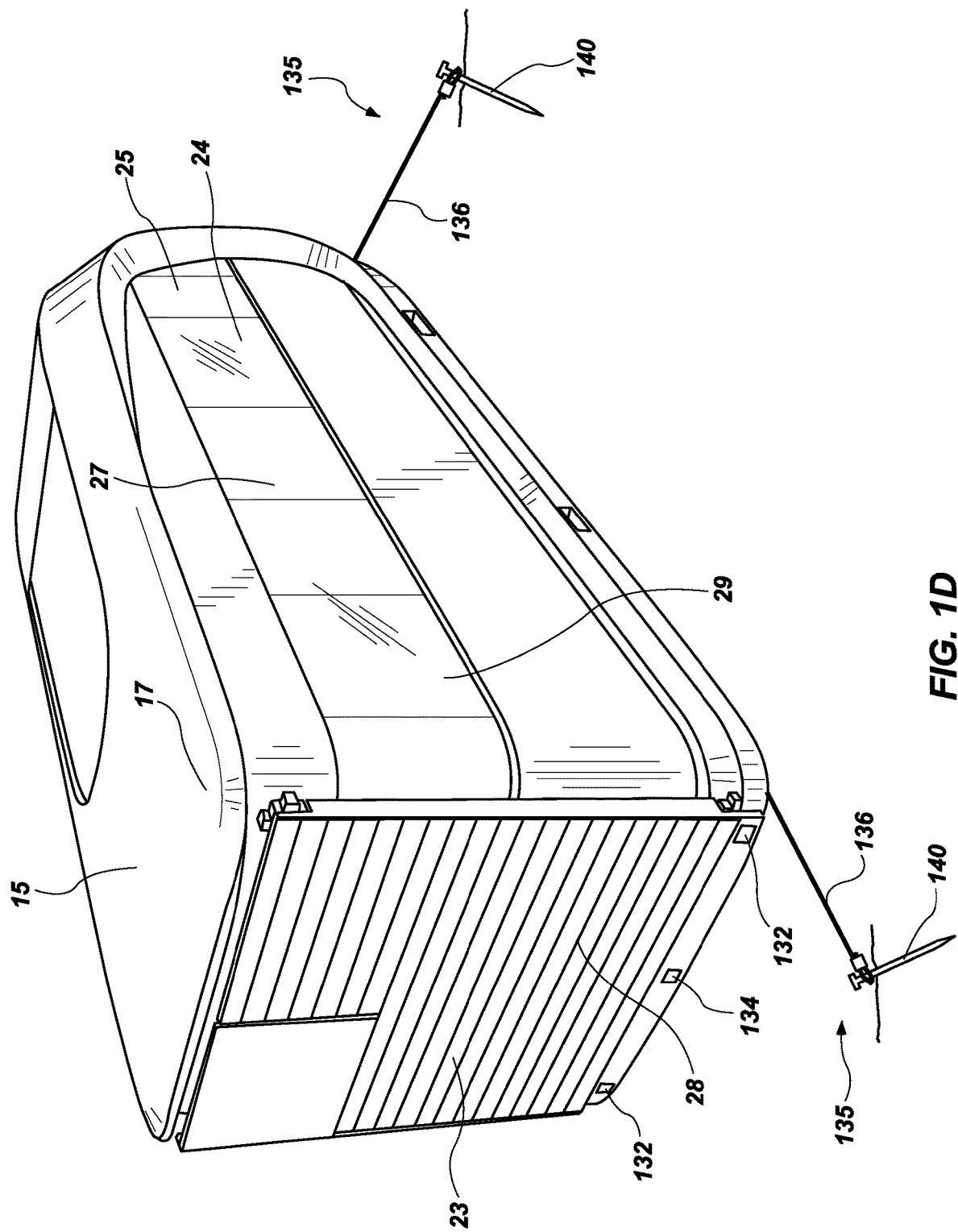
FIG. 1D is an elevated perspective view of the front of the residential unit of FIG. 1.
Figure 1E:
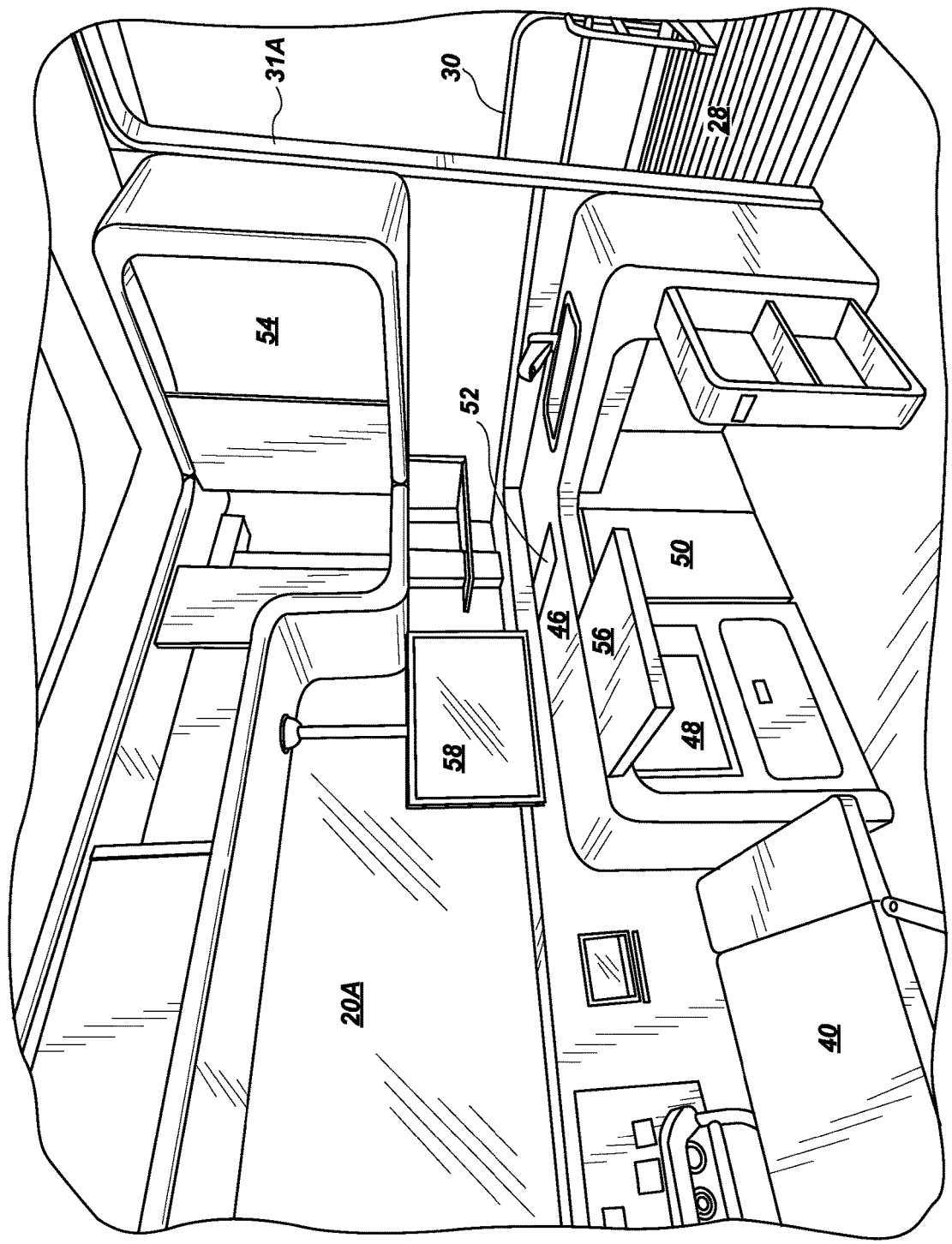
FIG. 1E is a sectional view of the kitchen portion of the residential unit interior.
Figure 1F:
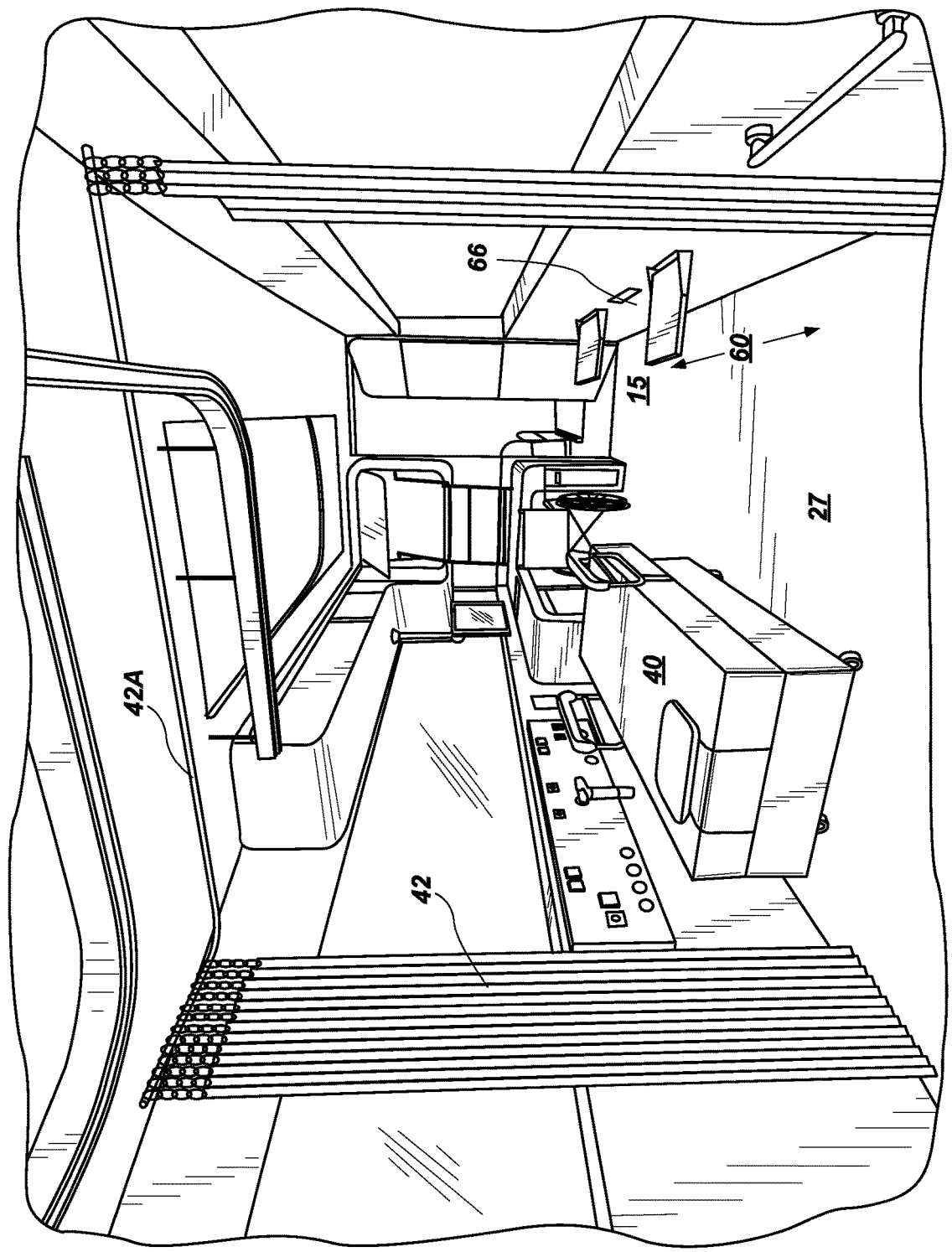
FIG. 1F is an elevational sectional view of the residential unit interior.
Figure 1G:
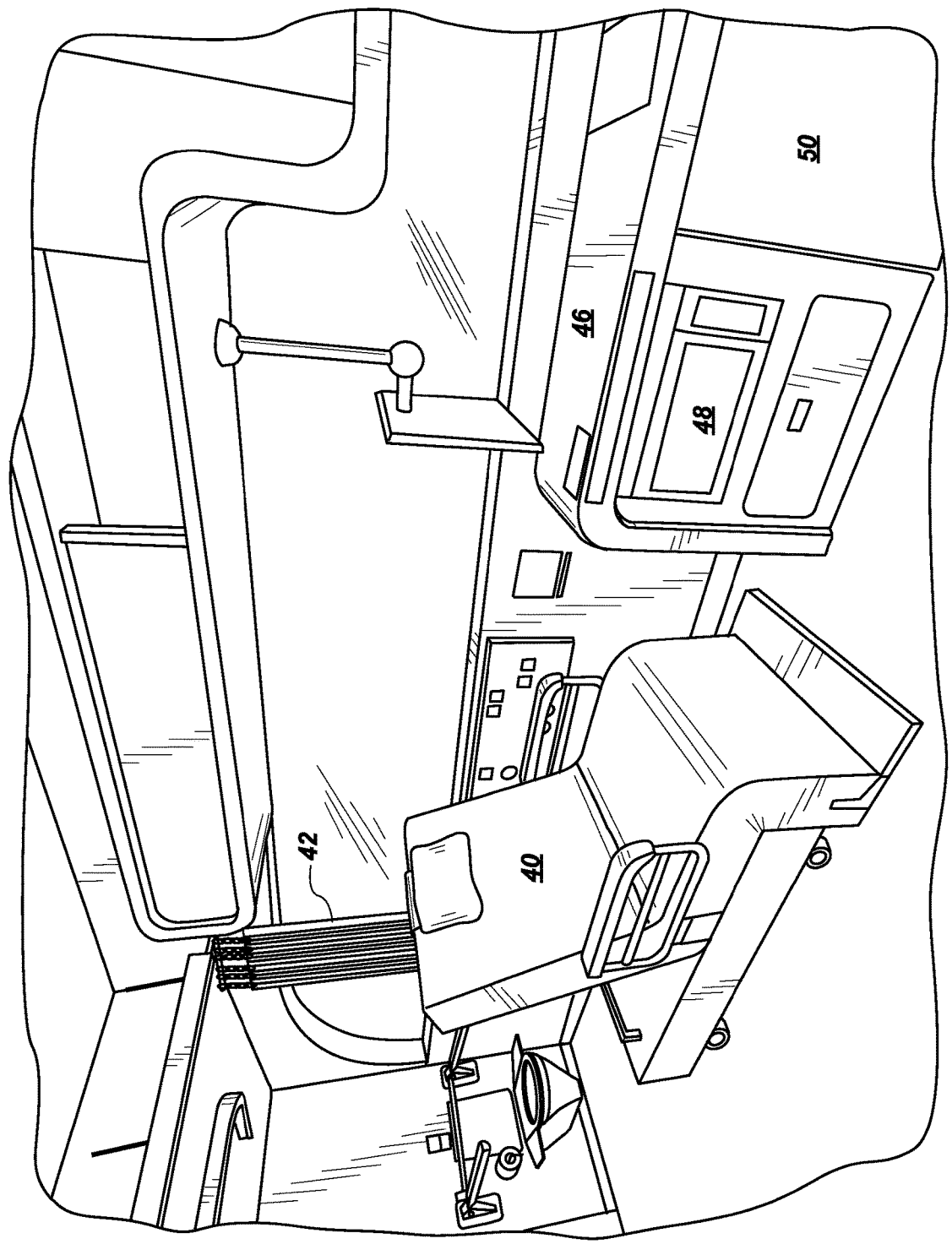
FIG. 1G is a perspective sectional view of the interior of the residential unit showing the bedroom portion of the interior.
Figure 1H:
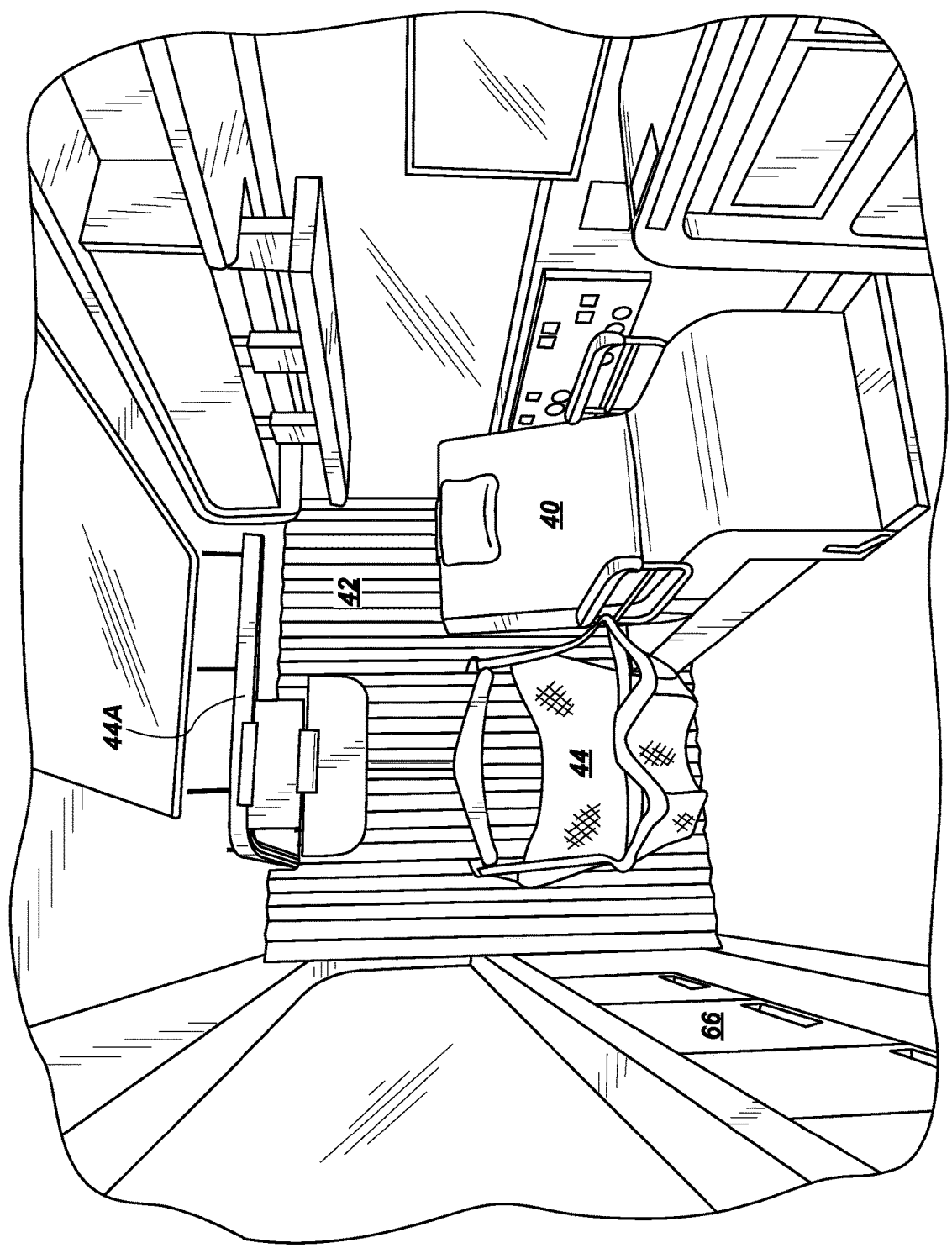
FIG. 1H is a sectional view of the interior of the residential unit showing the bedroom portion of the interior.
Figure 1I:
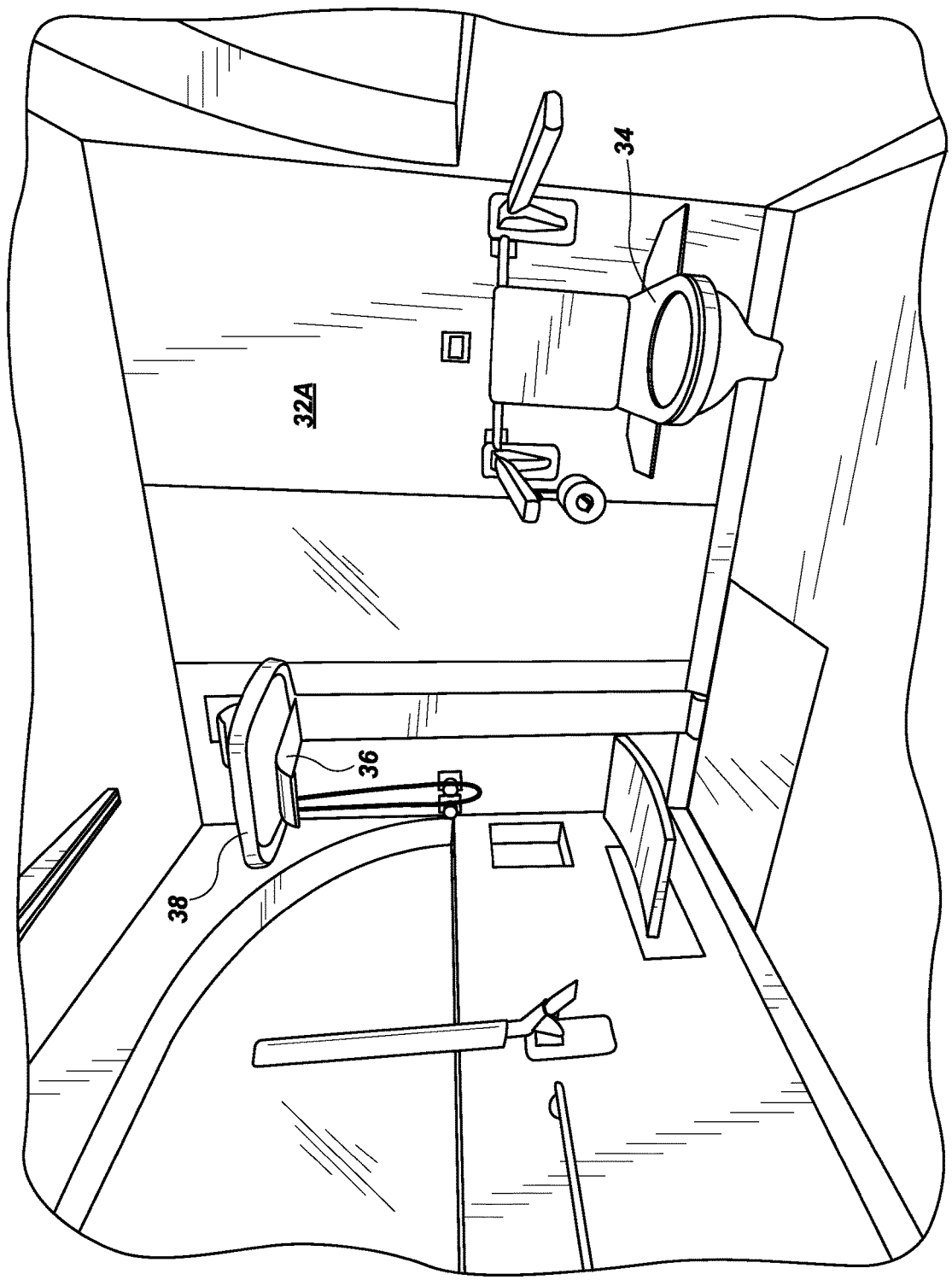
FIG. 1I is a sectional view of the interior of the residential unit showing the bathroom portion of the interior.

As shown in FIG. 1 et seq. of the drawings a residential unit 15 of the instant invention may include a metal alloy frame 17 which may include a steel base frame element 18. The frame 17 is largely, if not completely, encased within an enclosure 19. In a preferred aspect of the invention the frame assembly includes a metal alloy frame and a conjoined steel base. In some constructions composite materials may be utilized. Notably the unit may be manufactured without the use of wood in its structural framework.

Due to the use of metal and composite materials, the residential unit is anticipated to have an approximately use life of between 30 to 40 years. It anticipated that this long use life will facilitate the unit's being leased to a number of sequential occupants thereby providing a lower cost residential housing option for patients requiring residential care at affordable pricing. Instead of an occupant purchasing the unit outright, it is anticipated that the unit can be leased thereby reducing the upfront cost to the occupant. By allowing an occupant to avoid upfront costs, it is anticipated that the unit will permit an occupant to save between $75,000-$150,000 in costs. The residential unit thereby leads to a substantial savings of between 40-70% over current residential care centers in monthly costs. Furthermore, when the occupant is no longer in need to the unit, any lease payments cease as the unit is returned to its provider. It is refurbished as new and sent back out to another client.

The enclosure may be fabricated from a composite material such as fiberglass or laminate. In the illustrated embodiment the enclosure is a one piece structure, which may be slipped over the frame 17 during construction. The frame 17 and the enclosure 19 form a generally sealed, water tight assembly which surrounds a hollow interior, which, in turn, defines a residential space for the unit's occupant. In a preferred embodiment as shown, the unit is organized around a generally rectangularly configured floor plan. The unit defines a first end 21, an opposing second end 23 and two upstanding sidewalls 24, positioned parallel to one another and interconnecting the opposing first and second ends.

In preferred constructions the residential unit is sized to be transported (two units) legally on a standard 53 foot flat-bed trailer. In a further preferred construction, each unit obtains an external length of approximately 24 feet and a width of approximately 8 foot 6" (legal width) 102" hereby permitting two units to be transported simultaneously on the same flat bed trailer. Although the indicated dimensioning is preferred, larger units are within contemplation should they be necessary to provide for specific occupant's requirements. Since the unit may be transported to its use situs on a flat-bed trailer, the first end of the unit 21 may be configured to define a sleek aerodynamic exterior surface which contributes to rendering the transportation of the unit on a flat-bed trailer more efficient. The first end 21 of the unit may be positioned on the flat bed toward the cab of the truck transporting the unit and thereby forms a leading edge for the unit facing into the direction of travel.

The second end 23 includes a door 31 configured to provide access into the interior of the unit. The door may be offset from the center of the end 23 and made accessible by a removable aluminum ramp which is fitted with hand rails. In a preferred construction the door is approximately 40 inches wide and compliant with the provisions of the American Disabilities Act (ADA). The door 31 is preferably fitted with an air tight seal kit about its perimeter. An important consideration in the design of the residential unit is the possibility that the area where the unit may be sited during its use may be subjected to flooding conditions. In anticipation of such a possibility, the residential unit has been designed to float when it is surrounded by flood water. Since the enclosure forms a water tight association with the frame and the door is fitted with an air tight seal about its perimeter, the residential unit is sealed against the entry of water into the unit's interior. Moreover, as will be explained in detail later, the residential unit 15 is typically simply placed on the underlying ground surface without any further securement of the unit to the ground surface. It follows that if an upwardly directed force is applied to the unit, as for example that attributable to the buoyancy of the unit in water, the unit will be lifted upward away from its position on the ground surface and will become a floating vessel thereby contributing to the safety of the occupant and protection of the unit due to water damage. Furthermore, due to its construction, the residential unit is sealed to preclude entry of water into the unit's interior thereby providing some additional security to the occupant.

The upstanding sidewalls 24 of the unit are shown fitted with windows 28 which not only admit light into the interior of the unit for the occupant's comfort and enjoyment, but also permit the occupant to look outward and give them a more spacious sense of being with the environment surrounding the unit. In preferred constructions windows 28 may be fitted to selectively changeable privacy glass which permits the occupant to vary the tint and frosting of the glass at will and thereby control the visual accessibility of the unit's interior to persons positioned outside of the unit.

The residential unit contemplates an open interior plan. Anticipating a wall thickness of 6 inches, a preferred construction of the residential unit contemplates an internal width of 7.5 feet, inside height of 7.5 feet and an inside length of 23 feet of the interior of the unit.

Figure 8:
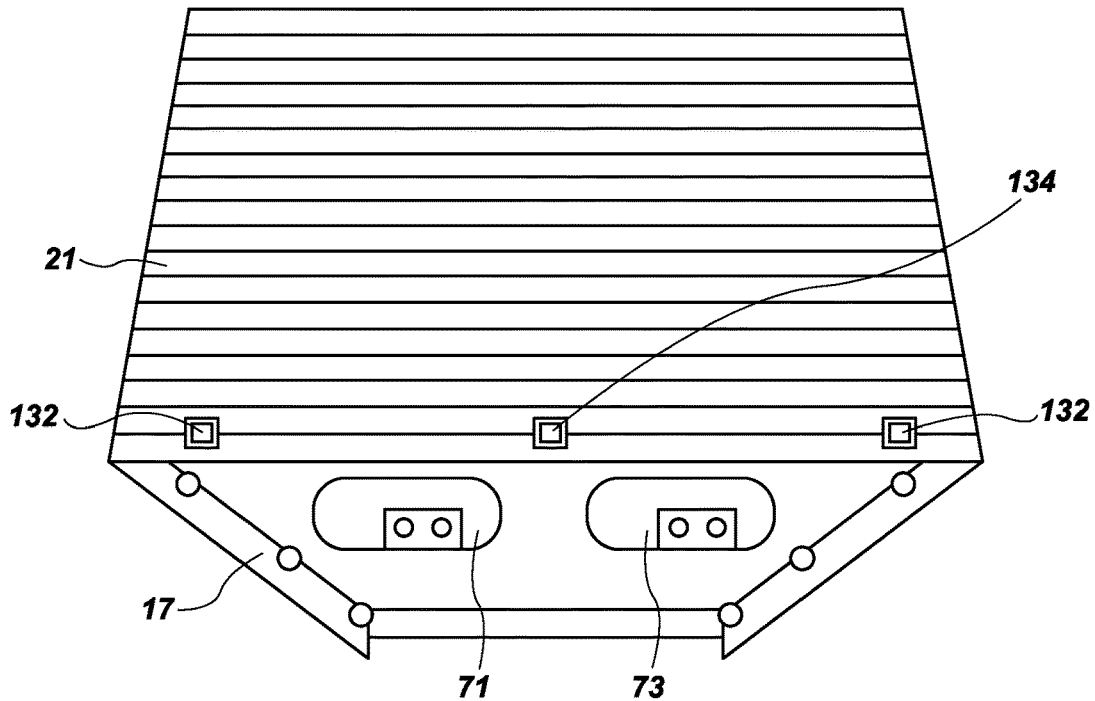
FIG. 8 is a rear perspective view of the residential unit showing the mounting location of the grey and black water reservoirs.

Bathroom facilities 25 are preferably located proximate the first end 21. In close proximity to a mechanical room in nose of unit. Not only does this positioning distance the bathroom from the kitchen area 29 due to sanitation concerns, but furthermore, as shown in FIG. 8, the invention contemplates positioning the waste water reservoirs for the unit 15 proximate the first end 21. Locating the bath facilities near the first end 21 therefore positions the toilet, shower and sink proximate the reservoir which is provided to receive and collect waste water from each of those appliances. The central region 27 of the unit 15 is reserved for a bedroom and living room, which may be furnished with a bed which is convertible to a chair. The bathroom facilities 25 may be isolated from the central region 27 by a displaceable privacy curtain.

A kitchenette and telemedicine portal section is located proximate the second end 23. In one construction the galley section will be dimensioned to be approximately 6 ft. long by 7.5 ft. wide. Constructed to be ADA compliant, the kitchenette may include a counter top, a built in microwave, and a refrigerator/freezer, which may be mounted under the counter to maximize the utilization of space. An induction cook top which utilizes a single or double burner may also be provided. A selection of cabinetry for providing storage space may also be provided in the kitchenette.

The kitchenette may also be configured to provide a desk area fitted with a telemedicine portal. The unit may be fitted with Internet connection or other forms of connectivity to provide a connection between the telemedicine portal an a professional care provider as well as the primary health care provider and (social connection capabilities with other family members, broadcasting of programming, and other connectivity. A GPS system may also be included in the unit for tracking and security purposes.

The kitchenette may also include corner cabinetry for use as kitchen storage. In a preferred construction the arrangement of the kitchenette is designed to provide a wheel chair corridor which extends along the complete length of the interior of the residential unit. In a preferred construction this corridor would extend along the left side of the unit's interior.

The central section of the interior is anticipated to provide a living room space which will also double as a bedroom. This section is preferably dimensioned to provide an open area of 8 feet by 7.5 feet. In order to enhance the occupant's wellbeing the ceiling in this central section may be configured to include a sunroof, preferably dimensioned to be 10 feet long by 4 feet wide. This sun roof, which may be fitted with selectably tinted glass, may be adapted to open and provide the occupant with access to the exterior of the unit. The sunroof, which in many ways simulates the construction of sun roofs in automobiles, may furthermore include a retractable door or cover which may be moved into position to conceal the glass of the sunroof. Given the positive effects attributable to exposure to sunlight, the residential unit has been designed to maximize the occupant's access to sunlight as well provide, solar passive benefits in warming during cold seasons or in colder environments. The unit may also be fitted with curved glass panels at the juncture of the sidewalls with the roof of the unit similar to the type of panels found on touring buses.

Various bed constructions are contemplated for use in the central section of the unit's interior. A temporary sleeping and seating arrangement for visitors may also be accommodated in the central section of the unit's interior. This arrangement, illustrated in FIGS. 4-7 will be described subsequently in more detail. This arrangement may be built into the wall of the central section and arranged to fold down into the central section. In a preferred construction these temporary seats may be mounted on the wheel chair corridor side of the central section of the unit's interior.

Preferably dimensioned to be approximately 5 feet long by 7.5 feet wide, the bathroom/Shower section of the unit's interior is positioned toward the first end of the unit's interior. This particular area will be isolated from the living room area by a movable privacy curtain. This section will be preferably furnished with a vacuum flush toilet, bidet, a sink, and shower with vacuum drain, all of which will be ADA compliant. In preferred constructions a vertically displaceable sink, of the type conventional sold under the trademark LIFT may be utilized to optimize the usage of space within the bathroom.

Positioned between the bathroom/shower section and the end 21 of the unit is a mechanical room. This room, preferably dimensioned to be approximately 4 feet long by 7.5 ft. wide will house the heating, ventilation and air conditioning equipment as well as the fresh water reservoir and waste water reservoir, air filtration system, hot water heater and other mechanical systems of the unit. The mechanical room is preferably separated from the Bathroom by a wall fitted with panels for accessing and facilitating servicing and repairing of those systems. The fresh water reservoir together with the grey and black water waste reservoirs are rendered accessible through access doors defined in the exterior surface of the residential unit.

The bathroom/shower section may also be fitted with a ceiling mounted track system adapted for use with a sling arrangement adapted to transport a occupant by means of a sling from a wheelchair to the bed, to the shower or toilet.

The floor of the unit's interior may be provided to LED floor lighting similar to that found in modern aircraft as aisle lighting. This floor lighting is considered important in providing the occupant with guidance in reaching the bathroom facilities during the night without the need to activating the principal lighting system within the unit's interior. Entry into the residential unit is through a doorway 31A, which is fitted with a door 31 (not shown).

FIG. 1 also illustrates apparatus for transporting the residential unit 15 from a transporting flat bed truck to the selected location site as well as subsequently removing the residential unit from the location site and returning it to the flat-bed truck for purposes of its return to the unit's provider. An independently powered tug 33, adapted for transporting the residential unit, is releasably secured to the residential unit 15 at its end 23 by means of a bracket 34 mounted on the residential unit 15. The movement of the tug 33 is controlled by a user by means of a control mechanism located on an end of the tug. A bogie wheel assembly 35 is positioned on the opposing end 21 of the residential unit. The particulars of this bogie wheel assembly will be discussed later in more detail.

Figure 2:
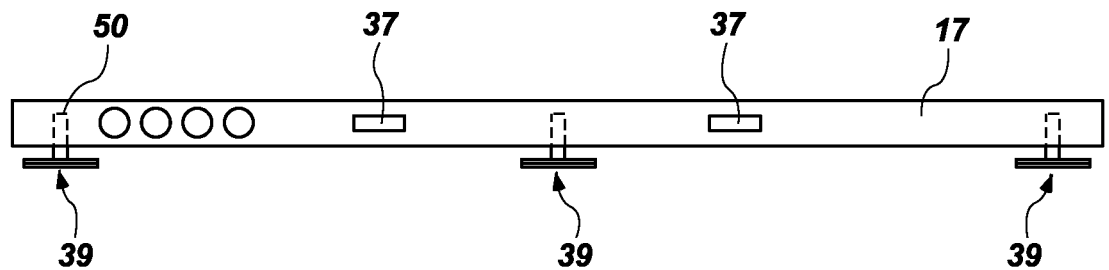
FIG. 2 is a sectional side view of the bottom of the residential unit, showing the height adjustable pads coupled with the frame of the residential unit.
Figure 3:
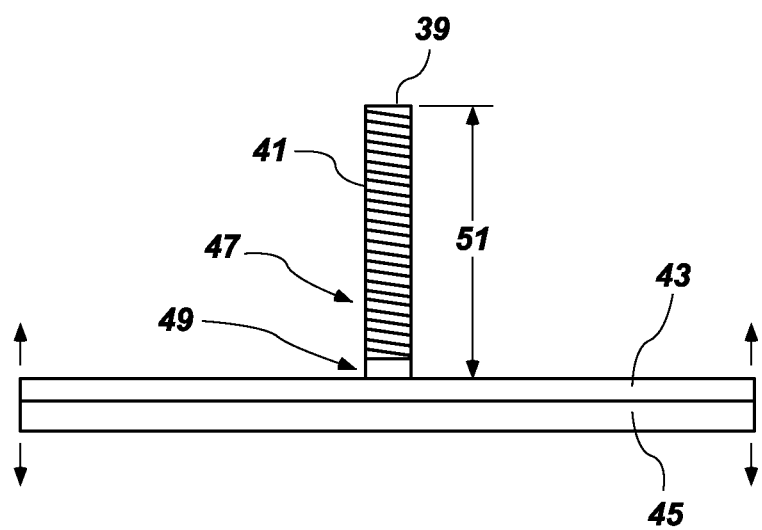
FIG. 3 is a side view of a height adjustable pad.

The residential unit 15 is positioned at a selected location by means of height adjustable pads 39. As shown in FIG. 2, pads 39 may be threadedly secured to the bottom of the frame 17 of the unit 15. The pads 39 are selectively positioned along a length of the frame 17 to provide a adequate support for the unit positioned above the frame 17. FIG. 3 illustrates one type of pad 39 which may be utilized in the invention. As shown pad 39 includes an upstanding shaft 47 having male threads 47 dimensioned to be threadedly received within the corresponding female threaded apertures 50 in the frame 17. A swivel 49 is positioned at the foot of the shaft 41 to provide for movement of the shaft 41 relative to a laterally extending pad foot 43, thereby permitting the unit 15 to be oriented at an angle to the plane of foot 43 other than 180 degrees. The bottom region of foot 43 is fitted with a high friction pad 45, which is preferably fabricated from rubber, but may also be manufactured from any material having a relatively high coefficient of friction similar to that of rubber. Pad 45 creates a friction based resistance to any horizontal movement of the pad 39 relative to the underlying ground surface. Notably, the pad 39 rests on the underlying ground surface without any further securement to the ground. Pad 39 functions not only to resist movement of the residential unit relative to the underlying ground surface, but furthermore, the pad 39 also functions to protect the underlying ground surface from damage should the unit be displaced.

In one aspect, the height adjustable pads include a ground engaging surface fabricated from a material, e.g. rubber, which exhibits a high coefficient of friction, e.g. static coefficient of friction greater than 0.5. The pads provide a stable electrically grounded mounting platform for the residential unit, but moreover, in part due to the frictional characteristics of the pads, the pads limit, if not preclude any horizontal movement of the residential unit relative to the underlying ground surface. Importantly, the residential unit is principally held in place on the pads by its weight and the frictional characteristics of the pads.

As noted previously, the absence of any fixed connection of the residential unit 15 to the underlying ground surface permits the unit 15 to rise with any flood waters, in coastal or low lying areas, which may surround the residential unit during its use, due to the buoyancy of the unit.

In an alternative aspect of the apparatus, adapted specifically for those instances in which the residential unit is to be located in a geographic area which is subject to high winds, the residential unit may also be fitted with a supplementary ground securement system or tie down system 135. In one embodiment, these securement systems provide a series of ties 136, e.g. rope or wire ties, secured to the residential unit on one end and adapted for securement to the ground on their opposing ends for example by securement to pegs or screws 140 adapted to be driven into the ground. These ties 136 provide an additional level of securement for the residential unit to the ground surface to retain the unit in place against the force of any wind applied to the surface of the unit. In those instances when the residential unit is in danger of being subjected to rising flood waters, this supplementary ground securement system is simply disengaged, thereby permitting the residential unit to float on the rising waters and consequently provide a level of safety to its occupant.

Figure 4:
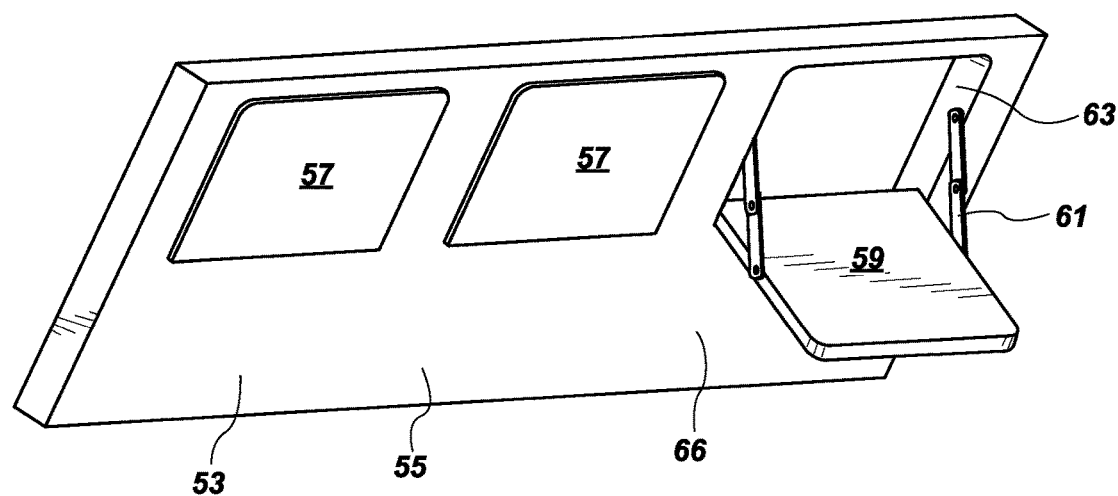
FIG. 4 is a perspective view of a combination sleeping bed and seating arrangement for the temporary accommodation of a primary health care provider within a residential unit, showing the bed in a retracted stored condition.
Figure 5:
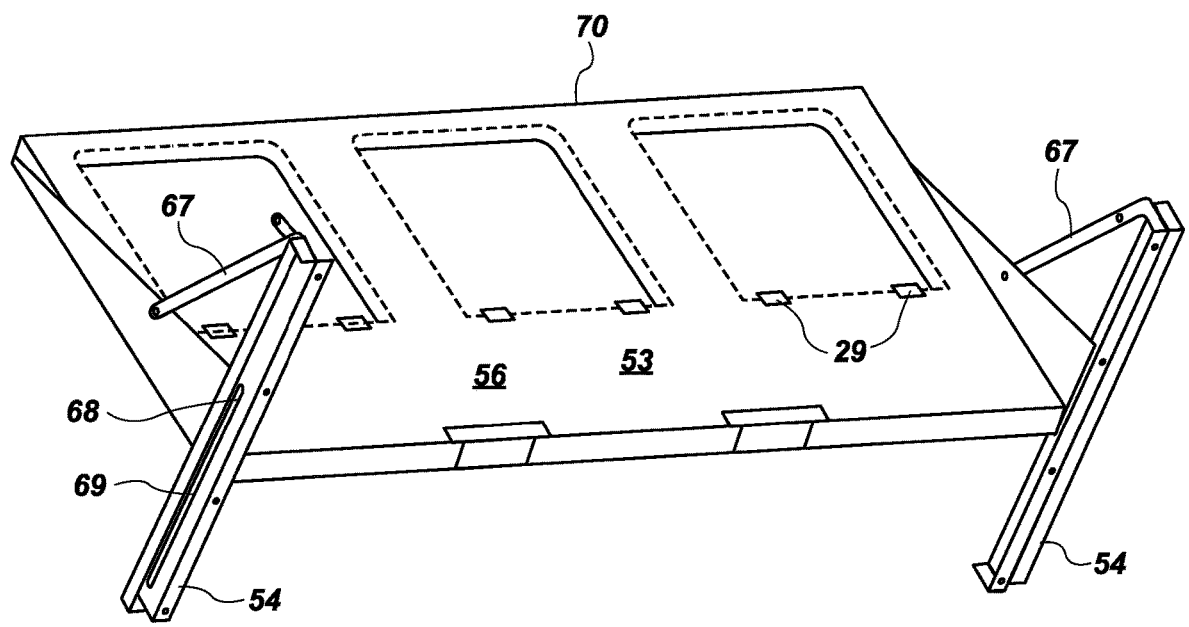
FIG. 5 is a bottom perspective view of the combination sleeping bed and seating arrangement of FIG. 4.
Figure 6:
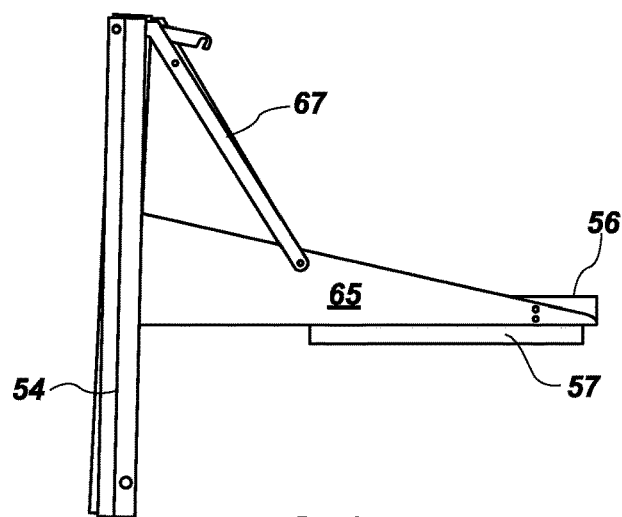
FIG. 6 is a side view of the combination sleeping bed and seating arrangement of FIG. 4.
Figure 7:
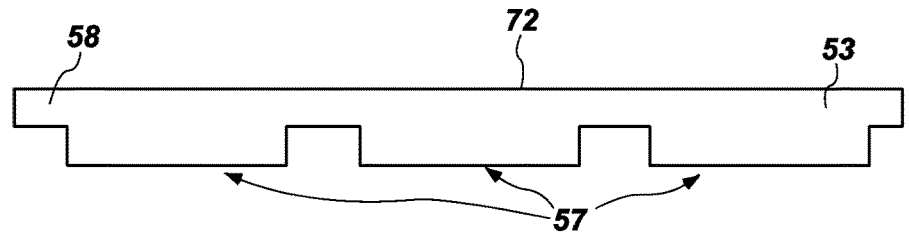
FIG. 7 is a section view of the combination sleeping bed and seating arrangement of FIG. 4.

FIGS. 4-7 illustrate a combination bed and seating arrangement which may be fitted within the interior of the residential unit. The bed and seating is intended for temporary use by a health care provider or visitor. The bed/seating arrangement is adapted to be retracted out of the way into a stored condition thereby opening up additional living space within the central region of the unit when it is not in use. As shown in FIGS. 4 and 5 the bed/seating arrangement includes an elongate support element 53. The bottom surface 55 of element 53 defines a plurality of openings 63, spacedly positioned along a length of the surface 55. Each opening 63 is dimensioned to receive a respective seat 57 which is hinged to element 53 by one or more hinges 62. Auxiliary supports 61 function to support an upper seating surface 59 of each seat 57 in an open use position. When the element 53 is positioned in an upright orientation against an interior wall of the unit's interior, each of the seats 57 may be rotated down into a use condition as shown in FIG. 4, about its respective hinges 62 whereby the seating surface 59 is made available for use by someone desiring to sit down.

FIG. 5 illustrates an orientation of the bed/seat combination in which the opposing surface 56 of the elongate element 53 is made accessible for use as a bed. As shown in FIG. 5 upright members 54, which are secured to the interior wall of the residential unit 15 are positioned to support the element 53 as that a free end 70 of element 53 is reoriented to extend outwardly into the interior of the residential unit from its positioning proximate the interior wall of the unit. Each member 54 defines an elongate upright channel or slot 69 therein into which a guide member 68 mounted on side panel 65 is slidably positioned. As the member 68 slides upwardly along the channel 69, the outer edge 70 of element 53 is rotated outwardly into the orientation shown in FIG. 5. Conversely, as the guide is displaced downwardly along the channel 69, the free edge 70 rotates back toward the sidewall of the unit until the element 53 is positioned adjacent to and parallel with the interior sidewall of the unit. A support brace 65 is secured at each end of the element 53 to which an auxiliary support brace 67 is rotatably mounted. An opposing end of each support brace 67 is rotatably mounted to a respective support 54. In the orientation shown in FIG. 5, the top surface 72 of element 53, defines a planar surface which can be fitted with a mattress to form a temporary sleeping surface.

FIG. 8 is a rear view of the residential unit showing the positioning of waste water reservoirs 71 and 73 within the enclosure of the unit. Propane storage tanks having a similar configuration to the waste water reservoirs may also be mounted on the residential unit, preferably on the underside of the unit, to provide a source of energy to the unit for cooking as well as heating during the winter months.

Figure 9:
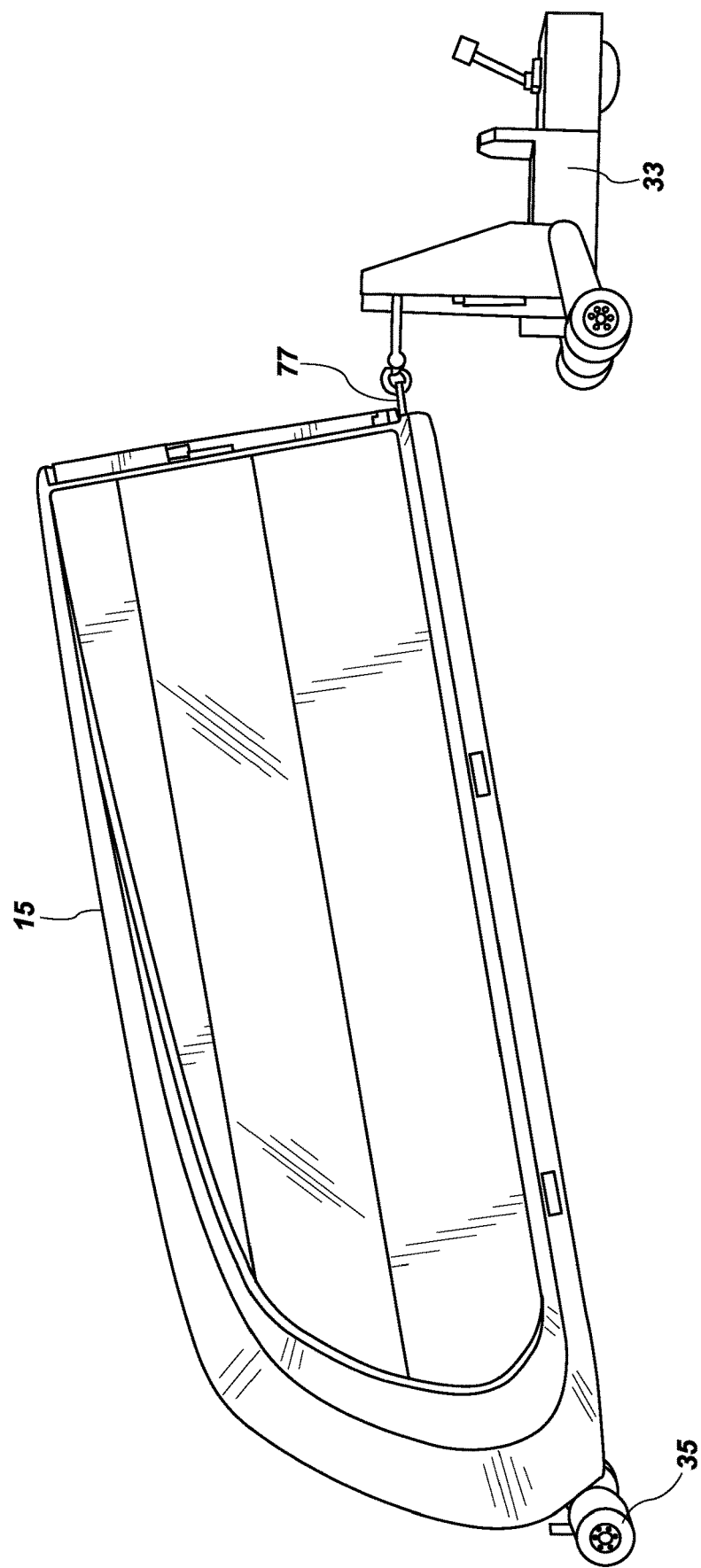
FIG. 9 is a side view of a residential unit in association with a transportation tug and bogie wheel assembly.
Figure 10:
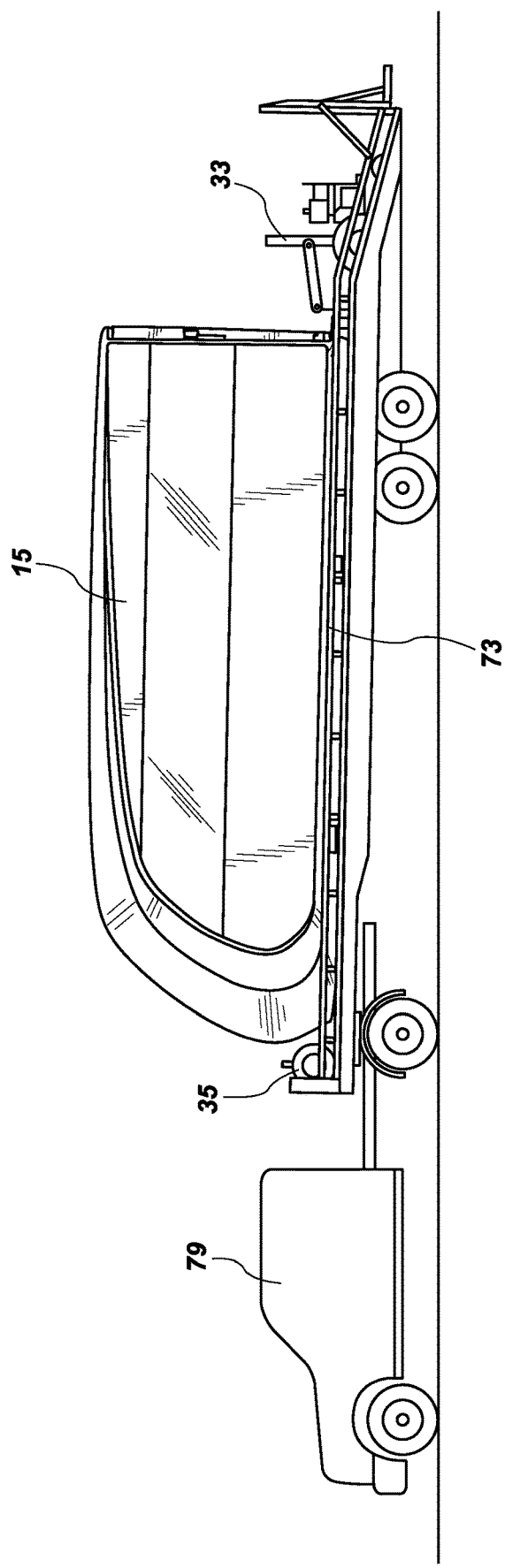
FIG. 10 is a side view of a residential unit mounted on a flat bed truck with an associated transportation tug.

FIGS. 9 and 10 depict the transportation of a residential unit 15 atop a flat-bed trailer 73 pulled by a tractor 79. A power tug 33 is shown stored at the end of the flat-bed trailer 73. Notably, the aerodynamically configured first end 21 of the unit 15 is shown positioned at the leading end of the trailer, proximate the tractor 79. In this position, the first end 21 of the unit provides a drag reducing profile to the unit is transported thereby reducing fuel consumption by the tractor 79.

Figure 11:
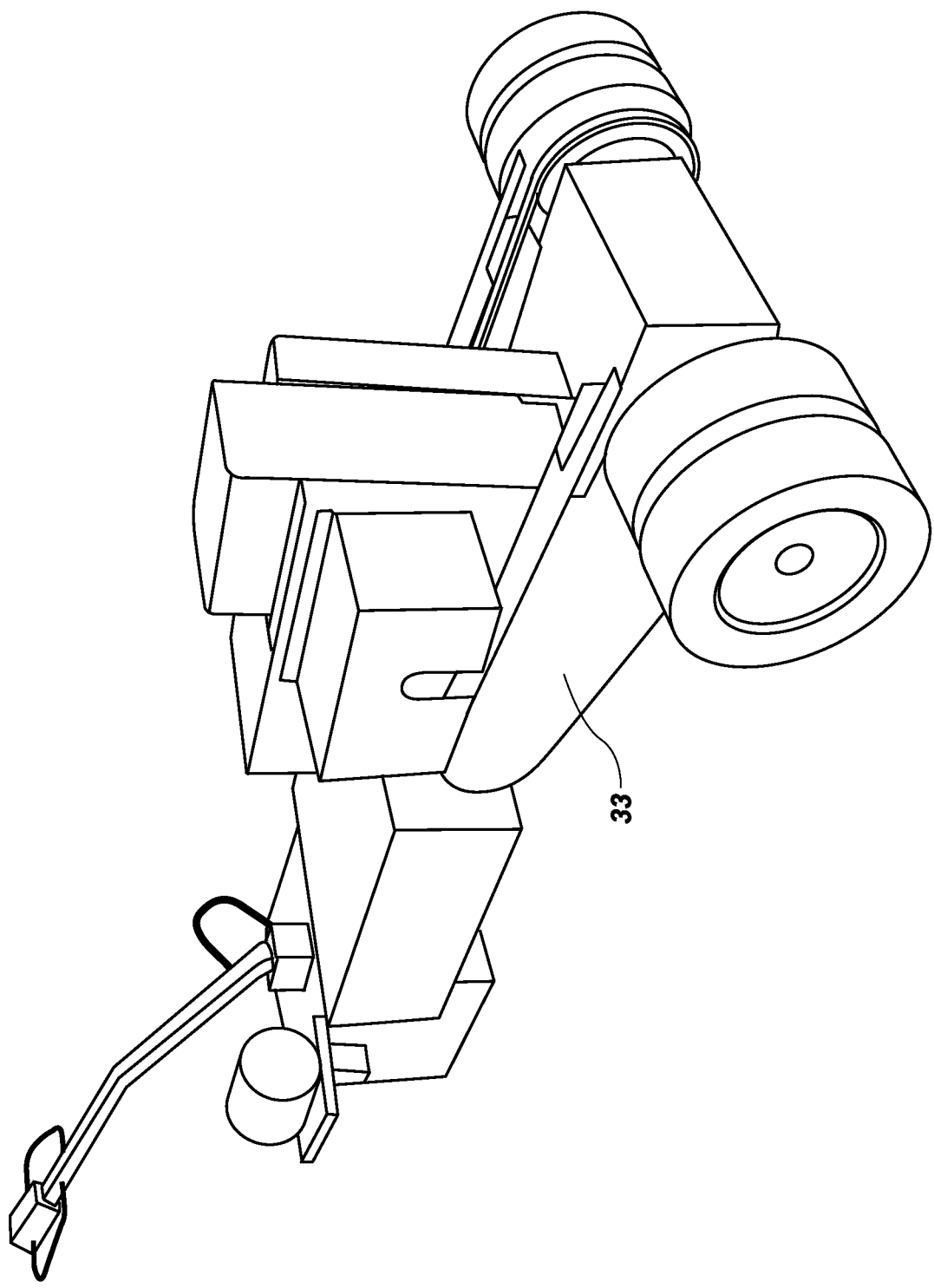
FIG. 11 is a perspective view of an alternative transportation tug.

A tug 33 is used to move the unit between the flat-bed trailer and the selected location site. An alternative tug construction which may be utilized in the instant invention is illustrated in FIG. 11. Upon arriving at the selected location at which the unit is to be positioned, with the bogie assembly 35 being positioned at end 21 of the unit 15 and the tug 33 being positioned proximate opposing unit end 23, the tug 33 pulls the unit off of the flat-bed trailer and thereafter maneuvers the unit 15 into its rest position at the preselected site. The lower portion of the residential unit may define a pair of openings 132 spacedly positioned from one another and adapted to receive and retain the bogie wheel assembly 35 during transport. A third opening 134 is adapted to engage with the power tug 33 to form a connection during the transport of the residential unit.

Figure 12A:
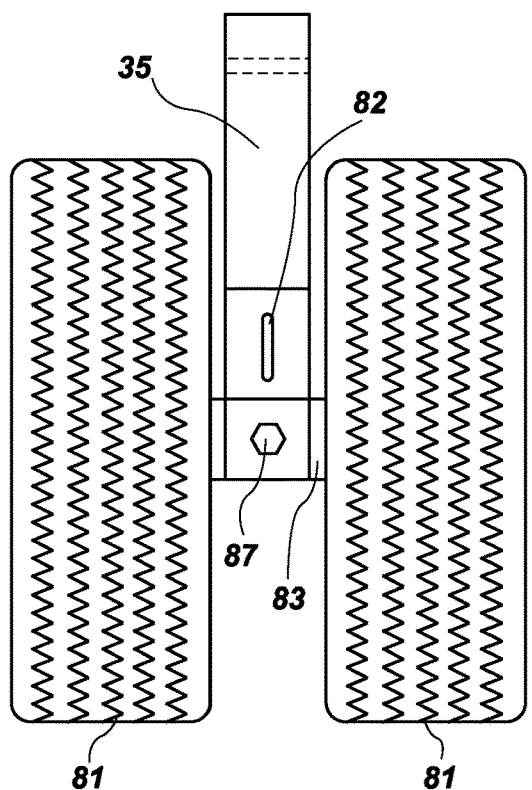
FIG. 12A is a top view of a bogie wheel assembly.
Figure 12B:
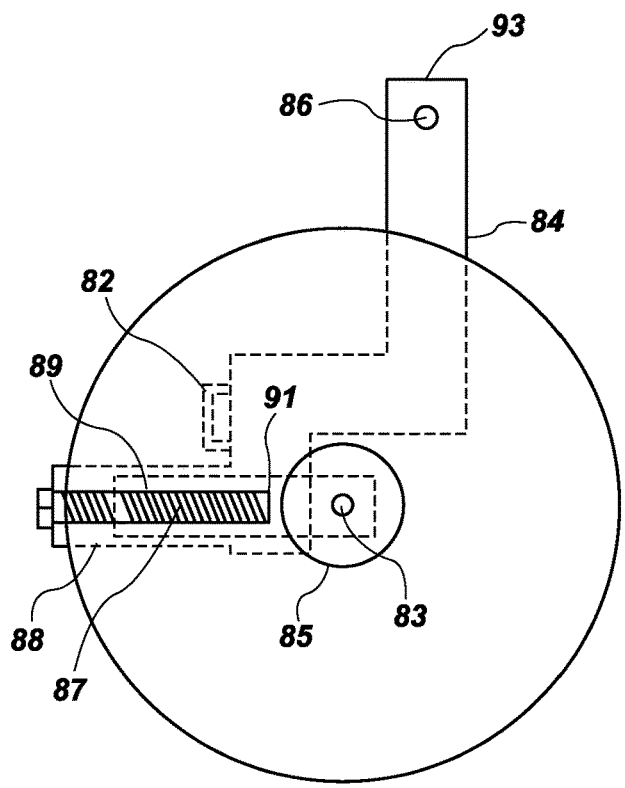
FIG. 12B is a side view of a bogie wheel assembly.

The bogie assembly 35 is adapted to assist in carrying the unit 15 over uneven terrain. As may be seen in FIGS. 12A and 12B, the bogie assembly 35 includes a pair of parallel mounted wheels 81 secured to a common axle 83 journaled through a mounting assembly 85. A mounting arm 84 defines an aperture 86 adapted to facilitate connection of the bogie assembly to the unit 15. An opposing end 88 of the mounting arm 84 defines a female threaded channel 89 into which is threaded a male threaded bolt 87. The free end of bolt 87 is configured to engage an powered impact wrench. As the bolt 87 is threaded into the threaded channel 89 the end 91 of bolt 87 engages the mounting assembly 85. Continued displacement of the bolt 87 into channel 89 causes the mounting arm 84 to be displaced upwardly, away from the mounting assembly 85, resulting in a concomitant raising or elevation of the unit 15 to which the free end 93 of the mounting arm is secured through aperture 86.

Figure 13:
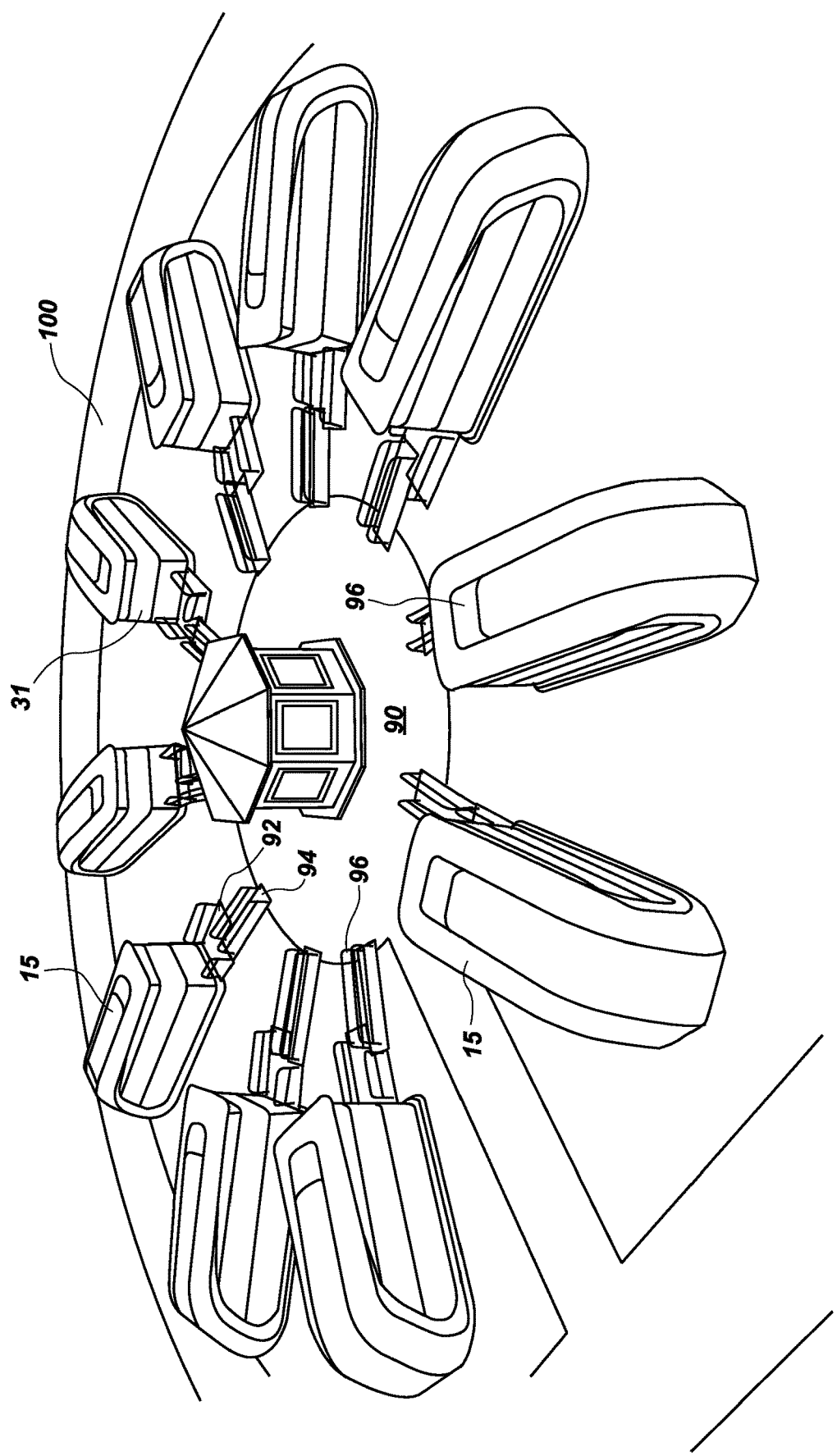
FIG. 13 is an elevated perspective view of a plurality of residential units secured in a spoke-like arrangement about a circular common area.

FIG. 13 illustrates a potential use of the instant invention wherein a plurality of residential units 15 are positioned in a spoke-like arrangement about a central circular shaped common area 90 to form a residential assisted living community. Each residential unit 15 is shown with an attendant deck 92 and a ramp 94 which leads from the common area 90 to the deck 92 of each residential unit. Both the deck and the ramp have upstanding railings positioned about their respective perimeters to provide a graspable support for those entering and leaving the individual units 15. The door 31 of each unit 15 is positioned contiguous to the respective deck of the unit.

As shown to advantage in FIG. 13 each residential unit 15 may include a sunroof 96 mounted in the roof of the unit. The sunroof may include a glass panel, which in some embodiments may be selectably tintable by the inhabitant to control not only visual accessibility to the interior of the unit but also the access of sunlight to the unit's interior.

An octogonally configured administration building is shown centrally positioned in the common area 90. The building has windows spacedly positioned about its perimeter sidewalls to provide an opportunity for the community's administrator to have a clear view of all of the residential units and thereby facilitate proper administration of the community. An access road 100 is also illustrated. Access road 100 is designed to provide access to the rear portion 21 of each unit, thereby facilitating access to the waste water reservoirs located in the rear portion of each unit.

Figure 14:
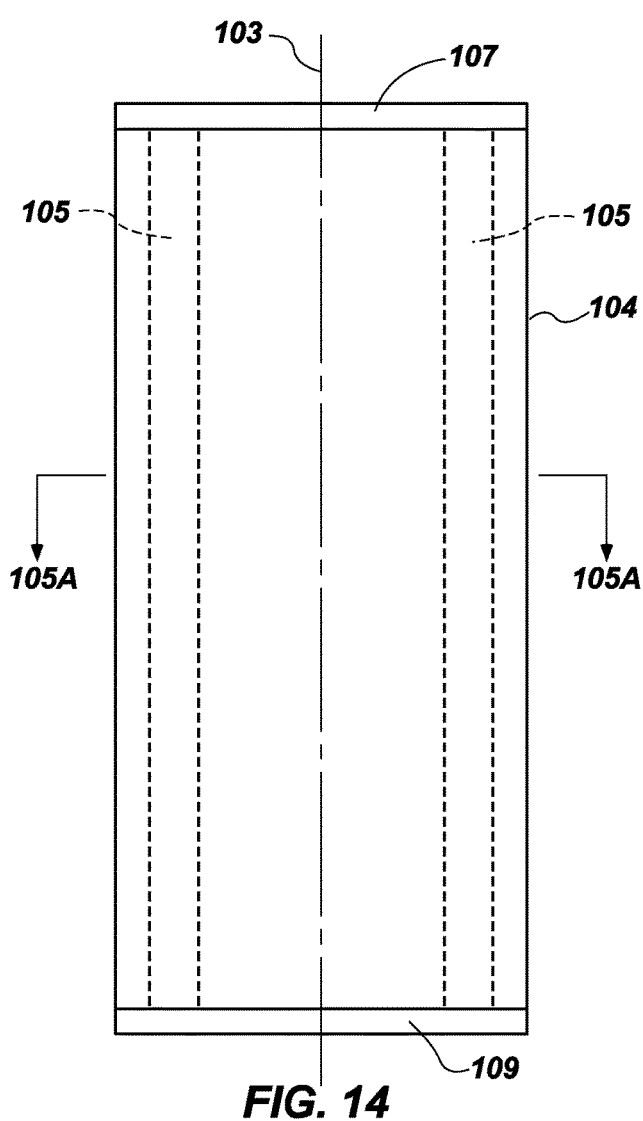
FIG. 14 is a side view of a pad housing adapted for mounting on the underside of a residential unit.

FIG. 14 illustrates a ground wave suspension system which may be fitted to the residential unit to protect the unit in the event of seismic disturbance or to provide a cushioned resistance both to an upward or downward motion of the residential unit. The ground wave suspension system may assist during the transporting of the residential unit either to or from its intended operational location. Furthermore, the suspension system may be utilized to protect the residential unit's occupants, the equipment housed within that unit as well as the residential unit itself from undo wear, sharp jarring and similar types of shocks.

The ground wave suspension system may also be used in place of the support pad 41 previous described to support a residency unit above an underlying ground surface. The ground wave suspension system may include a cylindrical housing 104 which supports a vertically extendable and retractable support assembly 106 mounted therein. The housing 104 may be welded to the residency unit, preferably on the underside of that residential unit to secure it in place relative to the residency unit. Alternatively, the housing 104 may be secured to the residency unit by a suitable bracket mounting or other means known in the art.

The support assembly 106, which is connected to a ground engaging support platform 43, may be displaced either upwardly or downwardly through a hollow channel defined within the interior of the housing 104, thereby altering the spatial relationship of the support assembly 106 to the housing 104 and consequently, the elevation of the housing 104 and its attached residency unit above the underlying ground.

Figure 15:
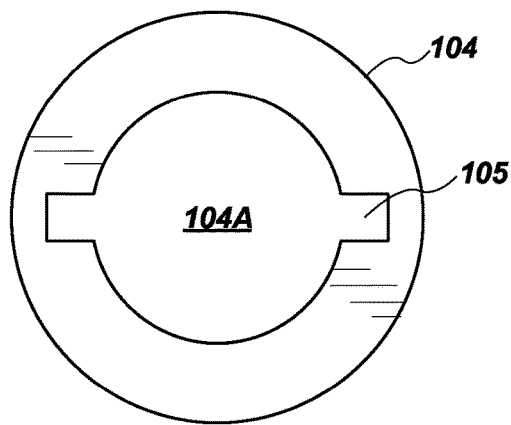
FIG. 15 is a cross sectional view of the pad housing of FIG. 14 taken along section lines 105A-105A.
Figure 16:
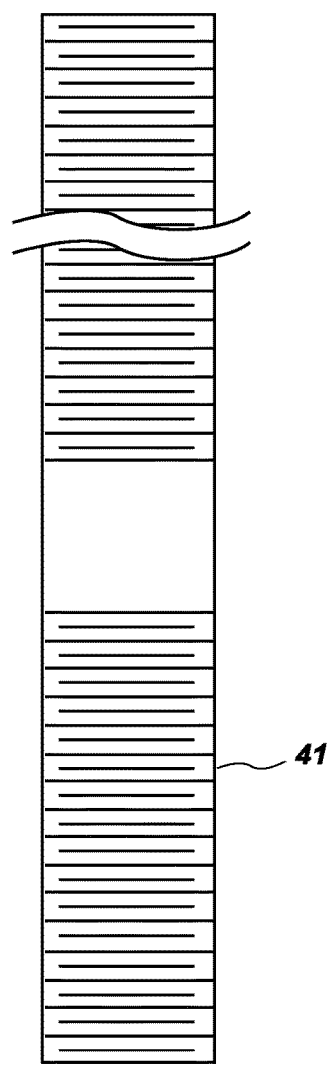
FIG. 16 is an exploded view of a portion of a threaded screw spring loaded assembly adapted for placement within the pad housing shown in FIG. 14.
Figure 16:
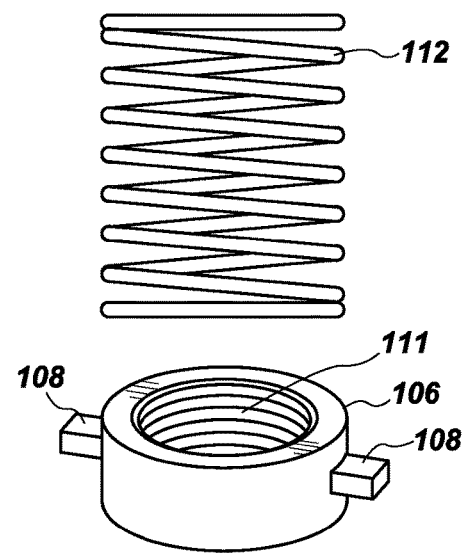
Figure 17:
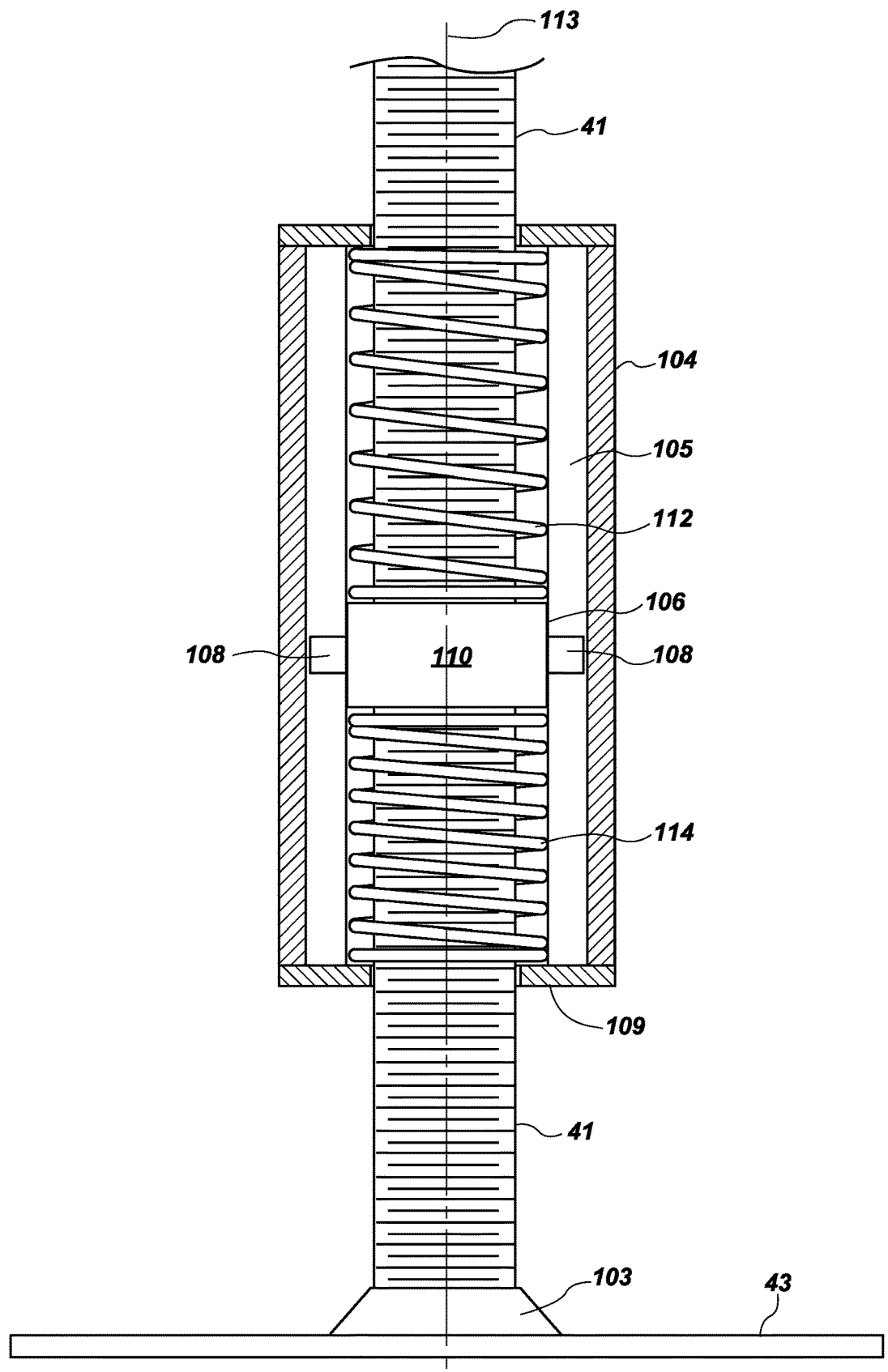
FIG. 17 is a cross sectional view of a spring loaded pad housing adapted for securement to the underside of a residential unit.

FIG. 15 illustrates a cross sectional view of the housing 104 taken along sectional lines 105A. As shown the cylindrically shaped housing 104 defines a cylindrical channel 104A which extends through the height of the housing 104, co-axial with the vertical axis 103 of the housing. A pair of generally square shaped cross section auxiliary channels 105 are defined within the interior sidewall of the positioned diametrically opposite one another about the perimeter of the channel 104A. Each of the auxiliary channels 105 extends vertically through generally the entire height of the housing 104, parallel with the vertical axis 103 of the housing. As shown to advantage in FIG. 17, a the vertical cross sectional view of the housing 104, a male threaded elongate support assembly 106 may be positioned co-axially within the housing 104, parallel to the vertical axis of the housing 104. The support assembly 106 includes a male threaded support shaft 41 which passes through a centrally positioned, circular opening defined in the end cap 107 of the housing. The support shaft 41 also passes through a centrally positioned circular opening defined in the opposing end cap 109. The support shaft 41 is secured to a mounting plate 103, by a swivel mounting. The mounting plate 103 in turn is secured to a base plate 43. The securement of the support shaft 42 to the mounting plate 103 is accomplished by use of a conventional swivel mounting which is known in the art.

A nut 110, which defines an internal channel therethrough, defines a series of female threads 111 along an interior sidewall of an internal channel defined within the nut 110. Extending outwardly from the exterior sidewall of the nut 110 is a pair of generally square cross sectioned ears 108 which are positioned diametrically opposite one another about the generally cylindrical external sidewall of the nut 110. Each of the ears 108 is dimensioned to be slidably received within a respective channel 105 defined within the interior sidewall of the housing 104. The engagement of the ears 108 with their respective channels 105 functions to guide the support assembly as it travels vertically upwardly and downwardly within the hollow interior channel of the housing 104.

A first helical spring 112 is mounted within the channel 104A. A first end of the spring 112 abuts against the internal sidewall of the end cap 107, while an opposing second end abuts against the upper horizontally positioned surface of the nut 110. A second helical spring 114 is positioned with the channel 104 whereby its first end engages a lower horizontally positioned surface 109A of the nut 110. A second end of the second spring 114 engages the interior sidewall of the second endcap 109. The threaded shaft 41 may be threadedly inserted into the nut 110 thereby adjusting the spatial distance between the threaded nut 110 and the platform 103, thereby adjusting the height of the residential unit above the underlying ground surface platform.

When a downwardly directed force is applied to the residential unit, the housing 104, due to its mounting on the residency unit, is directed vertically downward, thereby transmitting the force applied to the residential unit to the support assembly. Since the platform 43, is generally immovable due to its engagement with the underlying ground surface, the support assembly cannot be displaced downwardly with the housing 104. Instead, the housing 104 is displaced vertically downward, along its vertical axis, relative to the support assembly. The downwardly directed force is absorbed by the first helical spring 114, since the nut 110 is generally fixed into place along the height of the threaded shaft 41 due to its threaded engagement with that shaft 41. Concurrently, the downwardly directed force of the housing 104 releases a measure of the pre-existing force which has been imposed on the second spring 114, as the distance between the ears 108 and the end cap 109 increases as the housing 104 travels downwardly. The first spring 112 consequently generates an upwardly directed force against the interior surface of endcap 107 and by extension the residency unit through its interconnection with the housing 104. This upwardly directed force operates to serve to the correct the positioning of the residential unit to the position it enjoyed prior to the application of the initial downwardly directed force on the residential unit. Conversely, should an upwardly directed force be applied to the residential unit, the housing 104 would transit that force to the first spring 112, compressing that spring 112 and thereby producing a corrective force downwardly directed force by the first spring on the residential unit through the intermediation of the housing 104.

The support assembly 106 may be utilized to provide a cushioned resistance to forces applied to the residential unit either in a downward direction or an upward direction. Accordingly the support assembly 106 operates to cushion the residential unit from shocks which may result during the transport of the residency unit to its operational location or the occurrence any seismic activity proximate the residential unit's location. which may be applied to the residency unit thereby providing a cushioned resistance both in an upward and downward motion. Likewise the support assembly 106 protects the residential unit, its associated equipment, as well as its occupants from the normal shocks, wear and tear and dislocations which result from day to day operation of the residential unit.

The residential unit may be used effectively to isolate its occupant from pathogens within the ambit environment, or alternatively, the residential unit may be used to isolate an infected occupant from contact with others in the environment. The unit can be used effectively to preventive the spread of infectious disease like COVID-19 and other from our aging vulnerable members of society. In the context of isolating the occupant from pathogens within the environment of the residential unit, the residential unit may be fitted with a ventilation system, located in the mechanical room previously described, which is capable of creating a positive pressure environment within the residential unit whereby the air pressure within the residential unit exceeds the ambient air pressure. In those contexts in which the occupant may be infected and therefor there exists a need to isolate the residential unit's occupant from contact with those outside of the residential unit, the ventilation system may be adjusted to provide a negative air pressure within the living space of the residential unit relative to the ambient air pressure. Ventilation systems which may be installed within the residential unit and capable of creating the desired air pressure differentials are well known in the art.

The residential unit of this invention may also be adapted in some embodiments to function as a Class Q Quarantine Isolation unit. Such an isolation unit requires that the residential unit is adapted to provide negative pressure environment for isolating and accommodating highly infectious patients with pathogens such as those suffering from haemorrhagic fever and pneumonic plague. To meet the medical requirements of a Class Q Isolation Room the instant invention may be modified to provide a secure airlock fitted living space and isolation room within the residential unit. In one configuration the residential unit may be subdivided with a wall, having an sealed door mounted therein, be positioned within the residential unit to extend between the interior sidewalls of the residential unit and thereby isolate the bedroom area from the kitchen area. Such a subdividing wall effectively defines an isolation room, the kitchen area, and a living space, the bedroom. The door into the residential unit which provides access to the unit through entry way 31A may be fitted with an air seal door, similar that of the air seal door, mounted in the subdividing wall which separates the kitchen area from the bedroom area. The two air sealed doors may be interconnected through an interlock system, of the type known in the art, which precludes both doors from being positioned in an opened condition simultaneously.

A pressure monitor, of a type known in the art, is mounted within the bedroom portion of the residential unit to constantly monitor the air pressure within the bedroom and to signal an alarm should that the air pressure differential between the bedroom and the kitchen exceed pre-established limits. The alarm may be fitted with a time delay to avoid the alarm being sounded during normal entry and exit through the sealed door. Both the exterior door as well as the sealed door may be interlocking and fitted with a self-closing mechanism of the type known in the art, to thereby facilitate ease in entering and exiting the bedroom as well as the kitchen portions of the residential unit. As previously noted, the bedroom is fitted with an in suite shower and toilet may also be fitted with a clinical hand-wash basin with hands free operation. The kitchen, which functions as an isolation room in this context, may also be fitted with such a clinical hand-wash basin with hands free operation in order to meet medical guidelines. Further modifications of the residential unit to meet these particular requirements may include modifications to the air ventilation system of the residential unit to include with low level exhaust ducts located approximately 150 to 300 mm above floor level to facilitate waste air discharge from the residential unit discharge vertically to the outside air. A HEPA filter may be fitted to the exhaust ducts in order to properly filter the waste air. The ventilation system does not allow for return air being introduced into the residential unit. Given the current pandemic, the instant invention in this configuration offers an enhanced means of providing protection to the aged as well as other members of society who are most vulnerable to infection by the COVID-19 virus.

Figure 18:
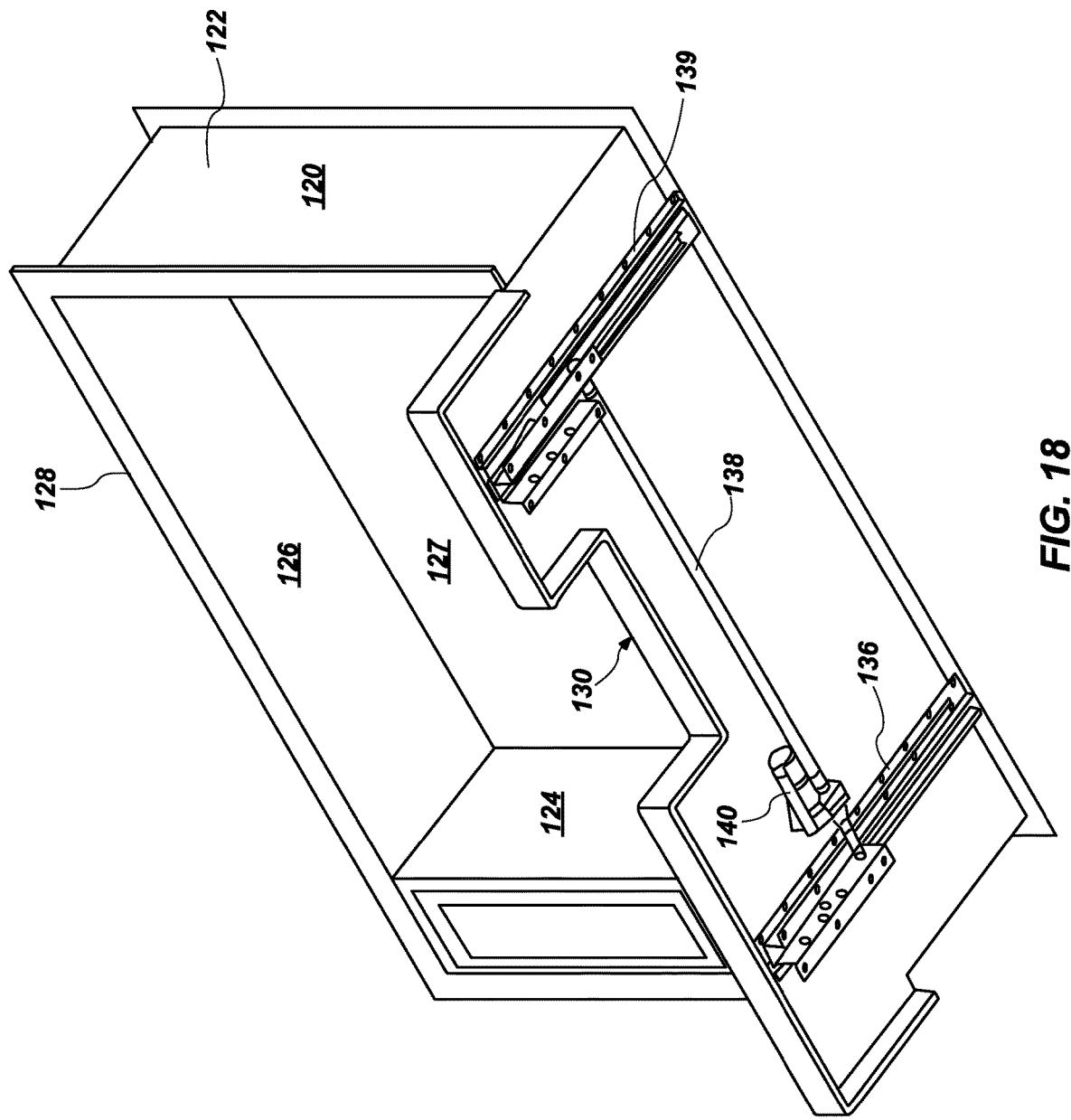
FIG. 18 is a perspective view of the drive mechanism of a laterally extendable side element of a residential unit.
Figure 19:
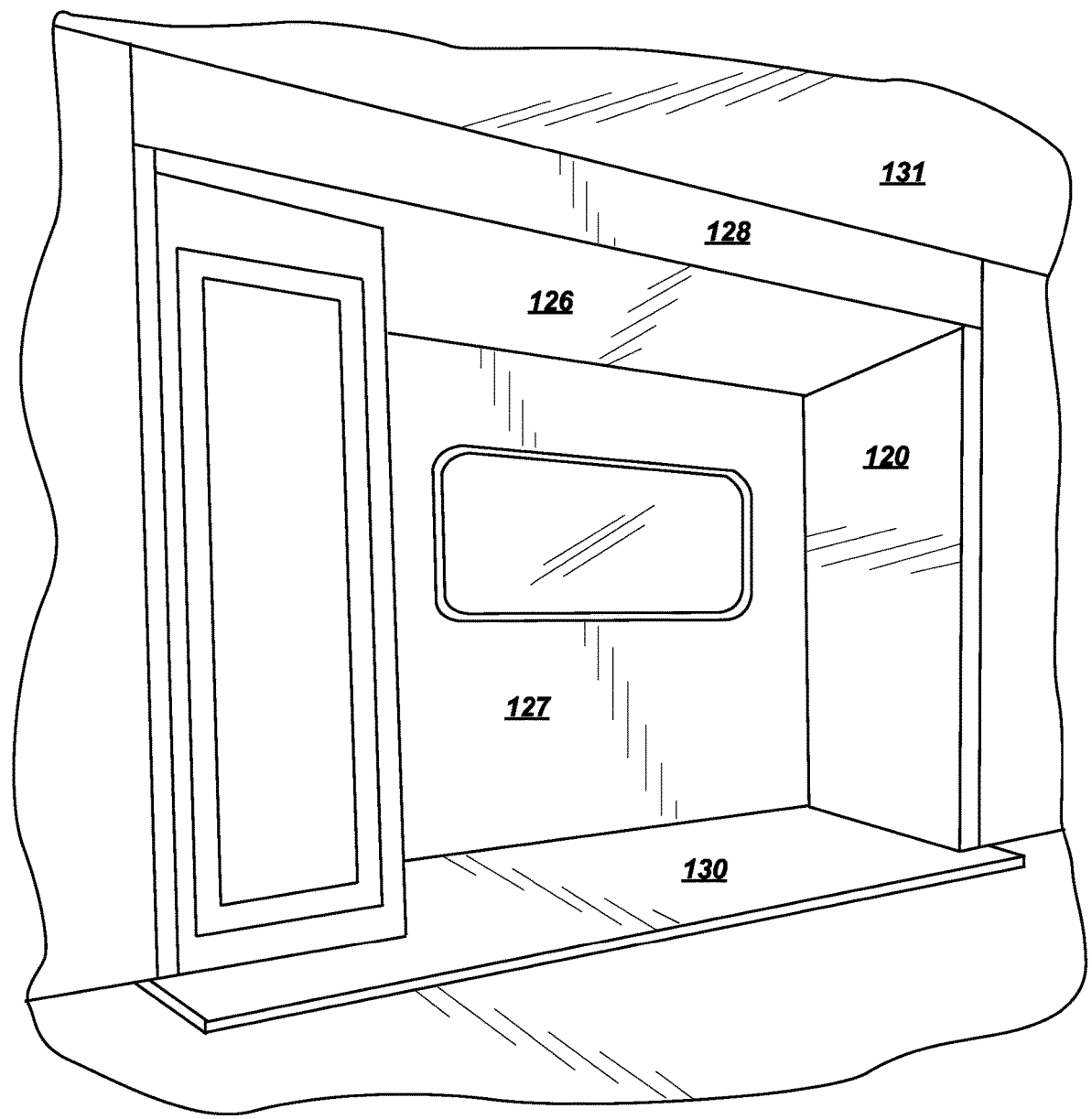
FIG. 19 is a perspective view of the laterally extending side element of a residential unit.

As shown in FIGS. 18 and 19, the residential unit invention may also include a further embodiment wherein a laterally extensile cabin 122 may be fitted to the sidewall of the residential unit to provide additional living space. FIG. 19 illustrates such an extensile cabin having a floor surface 130. A ceiling 126 is mounted on the upper ends of the sidewalls 124, 120 and 127 to define a generally enclosed living space. An entry portal 128 circumscribes the opening into the living space, having upright sidewalls 120 and 124 which extend upwardly from their securement to the floor 130. The cabin is displaced from a retracted position, wherein the living space is positioned largely located within the residential unit living space, defined by a residential unit which is not fitted with such an extensile cabin, to the extended condition shown in FIG. 19. This displacement may be accomplished by a drive mechanism 140 mechanically coupled or associated with a drive shaft 138. The drive rood is mechanically coupled to a drive assembly, of a type known in the art, which engages a pair of parallelly positioned drive tracks 134 and 136. Rotation of the drive shaft 138 operates to cause the extensile cabin to be displaced laterally along the tracks 134 and 136 in either an outwardly directed motion away from the main body of the residential unit or toward that residential unit. Various drive mechanisms and structural slideout arrangements are contemplated to achieve this particular embodiment of the instant residential unit. The particular drive mechanism and structural configuration of the slideout extensile cabin set forth in U.S. Pat. No. 5,788,306 to DiBagio et al is specifically identified as useful for this purpose. The disclosure of U.S. Pat. No. 5,788,306 is hereby incorporated herein in its entirety to supplement the instant disclosure of this feature.

Changes may be made to the aspects and embodiments described in this disclosure without departing from the broad inventive concepts they illustrate. Accordingly, this invention is not limited to the particular embodiments disclosed, but is intended to cover all modifications that are within the scope of the invention as defined by the appended claims.

The invention claimed is:

1. A residential unit for use by a patient requiring medical assistance, said residential unit comprising:
    a metal frame having a base;
    a water-tight enclosure secured to said metal frame, said enclosure defining an interior,
    an air-sealed door for accessing said interior and a plurality of windows mechanically associated with said enclosure,;
    telemetric monitoring equipment, positioned within said interior for use in monitoring health related vital signs of a patient, resident within said interior, and thereafter relaying information regarding said vital signs to a health care provider located remote from said residential unit;
    a plurality of height adjustable pads, adapted for placement on a ground surface, said metal frame and enclosure being positioned on said pads and
    a tug for releasably coupling to said residential unit and transporting said residential unit over a ground surface to a preselected location.

2. The residential unit of claim 1 wherein said height adjustable pads are fabricated from a material having a high coefficient of friction, wherein said pads provide a nonpermanent mounting platform for said metal frame and enclosure above said ground surface which generally precludes any horizontal movement of said metal frame and enclosure over said ground surface.

3. The residential unit of claim 1 wherein said windows are fabricated from selectable privacy glass wherein a tint of said glass or frosting may be changed to control visual accessibility to said interior.

4. The residential unit of claim 1 wherein said enclosure is fitted with an environmental control system adapted for controlling the temperature and air pressure within said interior.

5. The residential unit of claim 1 wherein said enclosure is fitted with storage means for receiving and storing waste water produced within said residential unit.

6. The residential unit of claim 1 further including a tie down system, adapted to engage with said frame and said ground surface to provide a securement of said residential unit and said ground surface.

7. The residential unit of claim 1 further comprising a temporary sleeping accommodation for a health care provider, said sleeping accommodation being retractable into an upstanding wall of said enclosure, said temporary sleeping accommodation further including a plurality of seating structures configured to fold out from said accommodation when said temporary sleeping accommodation is positioned in a closed orientation.

8. The residential unit of claim 1 further comprising a bogie for use with said tug for releasably coupling with said residential unit and transporting said residential unit over a ground surface to a preselected location.

9. A residential unit for use by a patient requiring medical assistance, said residential unit comprising:
    a metal frame having a base;
    a water-tight enclosure secured to said metal frame, said enclosure defining an interior,
    an air-sealed door for accessing said interior and a plurality of windows mechanically associated with the enclosure,
    telemetric monitoring equipment, positioned within said interior for use in monitoring health related vital signs of a patient, resident within said interior, and thereafter relaying information regarding said vital signs to a health care provider located remote from said residential unit;
    a plurality of height adjustable pads, adapted for placement on a ground surface, said metal frame and enclosure being positioned on said pads, and
    a temporary sleeping accommodation for a health care provider, said sleeping accommodation being retractable into an upstanding wall of said enclosure, said temporary sleeping accommodation further including a plurality of seating structures configured to fold out from said accommodation when said temporary sleeping accommodation is positioned in a closed orientation.

10. A residential unit for use by a patient requiring medical assistance, said residential unit comprising:
    a metal frame having a base;
    a water-tight enclosure secured to said metal frame, said enclosure defining an interior,
    an air-sealed door for accessing said interior and a plurality of windows mechanically associated with said enclosure;
    telemetric monitoring equipment, positioned within said interior for use in monitoring health related vital signs of a patient, resident within said interior, and thereafter relaying information regarding said vital signs to a health care provider located remote from said residential unit; and
    a plurality of height adjustable pads, adapted for placement on a ground surface, said metal frame and enclosure being positioned on said pads;
    a ground wave suspension system comprising:
        a plurality of housings spacedly secured to the metal frame proximate a lower surface of said residential unit, each housing defining a vertically positioned, hollow channel and a pair of oppositely positioned, vertically positioned auxiliary channels, said housing further including a first endcap and a second endcap, said endcaps being secured to opposing ends of said housing;
        each said housing having a threaded shaft positioned within said hollow channel for displacement upward and downward within said channel relative to said housing;
        each said threaded shaft having a threaded nut threadedly mounted thereon for threaded displacement along a height of said threaded shaft, each said threaded nut having a plurality of ears extending outwardly therefrom, each said ear being displaceably positioned within a respective auxiliary channel defined in the housing;
        each housing having a first spring mounted within said hollow channel and positioned between a first endcap and said threaded nut; and
        each housing having a second spring mounted within said hollow channel and positioned between a second endcap and said threaded nut;
        wherein each said threaded shaft is coupled to a respective said height adjustable pad,
    a tug for releasably coupling to said residential unit and transporting said residential unit over a ground surface to a preselected location;
    a bogie for use with said tug for releasably coupling with said residential unit and transporting said residential unit over a ground surface to a preselected location.

11. A residential unit for use by a patient requiring medical assistance, said residential unit comprising:

a metal frame having a base;

a water-tight enclosure secured to said metal frame, said enclosure defining an interior, an air-sealed door for accessing said interior and a plurality of windows mechanically associated with said enclosure, telemetric monitoring equipment, positioned within said interior for use in monitoring health related vital signs of a patient, resident within said interior, and thereafter relaying information regarding said vital signs to a health care provider located remote from said residential unit;

a plurality of height adjustable pads, adapted for placement on a ground surface, said metal frame and enclosure being positioned on said pads and a ground wave suspension system comprising:

a plurality of housings spacedly secured to the metal frame proximate a lower surface of said residential unit, each housing defining a vertically positioned, hollow channel and a pair of oppositely positioned, vertically positioned auxiliary channels, said housing further including a first endcap and a second endcap, said endcaps being secured to opposing ends of said housing;

each said housing having a threaded shaft positioned within said hollow channel for displacement upward and downward within said channel relative to said housing;

each said threaded shaft having a threaded nut threadedly mounted thereon for threaded displacement along a height of said threaded shaft, each said threaded nut having a plurality of ears extending outwardly therefrom, each said ear being displaceably positioned within a respective auxiliary channel defined in the housing;

each housing having a first spring mounted within said hollow channel and positioned between a first endcap and said threaded nut; and each housing having a second spring mounted within said hollow channel and positioned between a second endcap and said threaded nut;

wherein each said threaded shaft is coupled to a respective said height adjustable pad.

12. The residential unit of claim 9 wherein said height adjustable pads are fabricated from a material having a high coefficient of friction, wherein said pads provide a nonpermanent mounting platform for said metal frame and enclosure above said ground surface which generally precludes any horizontal movement of said metal frame and enclosure over said ground surface.

13. The residential unit of claim 9 wherein said windows are fabricated from selectable privacy glass wherein a tint of said glass or frosting may be changed to control visual accessibility to said interior.

14. The residential unit of claim 9 wherein said enclosure is fitted with an environmental control system adapted for controlling the temperature and air pressure within said interior.

15. The residential unit of claim 9 wherein said enclosure is fitted with storage means for receiving and storing waste water produced within said residential unit.

16. The residential unit of claim 9 further including a tie down system, adapted to engage with said frame and said ground surface to provide a securement of said residential unit and said ground surface.

17. The residential unit of claim 9 further comprising a tug for releasably coupling to said residential unit and transporting said residential unit over said ground surface to a preselected location.

18. The residential unit of claim 17 further comprising a bogie for use with said tug for releasably coupling with said residential unit and transporting said residential unit over said ground surface to a preselected location.

19. The residential unit of claim 11 wherein said height adjustable pads are fabricated from a material having a high coefficient of friction, wherein said pads provide a nonpermanent mounting platform for said metal frame and enclosure above said ground surface which generally precludes any horizontal movement of said metal frame and enclosure over said ground surface.

20. The residential unit of claim 11 wherein said windows are fabricated from selectable privacy glass wherein a tint of said glass or frosting may be changed to control visual accessibility to said interior.

21. The residential unit of claim 11 wherein said enclosure is fitted with an environmental control system adapted for controlling the temperature and air pressure within said interior.

22. The residential unit of claim 11 wherein said enclosure is fitted with storage means for receiving and storing waste water produced within said residential unit.

23. The residential unit of claim 11 further including a tie down system, adapted to engage with said frame and said ground surface to provide a securement of said residential unit and said ground surface.

24. The residential unit of claim 11 further comprising a temporary sleeping accommodation for a health care provider, said sleeping accommodation being retractable into an upstanding wall of said enclosure, said temporary sleeping accommodation further including a plurality of seating structures configured to fold out from said accommodation when said temporary sleeping accommodation is positioned in a closed orientation.

25. The residential unit of claim 11 further comprising a tug for releasably coupling to said residential unit and transporting said residential unit over said ground surface to a preselected location.

26. The residential unit of claim 25 further comprising a bogie for use with said tug for releasably coupling with said residential unit and transporting said residential unit over a ground surface to a preselected location.

27. The residential unit of claim 10 wherein said height adjustable pads are fabricated from a material having a high coefficient of friction, wherein said pads provide a nonpermanent mounting platform for said metal frame and enclosure above said ground surface which generally precludes any horizontal movement of said metal frame and enclosure over said ground surface.

28. The residential unit of claim 10 wherein said windows are fabricated from selectable privacy glass wherein a tint of said glass or frosting may be changed to control visual accessibility to said interior.

29. The residential unit of claim 10 wherein said enclosure is fitted with an environmental control system adapted for controlling the temperature and air pressure within said interior.

30. The residential unit of claim 10 wherein said enclosure is fitted with storage means for receiving and storing waste water produced within said residential unit.

31. The residential unit of claim 10 further including a tie down system, adapted to engage with said frame and said ground surface to provide a securement of said residential unit and said ground surface.

32. The residential unit of claim 10 further comprising a temporary sleeping accommodation for a health care provider, said sleeping accommodation being retractable into an upstanding wall of said enclosure, said temporary sleeping accommodation further including a plurality of seating structures configured to fold out from said accommodation when said temporary sleeping accommodation is positioned in a closed orientation.

* * * * *